US012678631B2

(12) United States Patent
Kim et al.

(10) Patent No.: US 12,678,631 B2
(45) Date of Patent: Jul. 14, 2026

(54) MEDICAL DEVICE WITH ENHANCED ELECTROCARDIOGRAM CHANNEL SELECTION

(71) Applicant: Physio-Control, Inc., Redmond, WA (US)

(72) Inventors: Jaeho Kim, Redmond, WA (US); Joseph L. Sullivan, Kirkland, WA (US); Robert P. Marx, Kent, WA (US)

(73) Assignee: Physio-Control, Inc., Redmond, WA (US)

( * ) Notice: Subject to any disclaimer, the term of this patent is extended or adjusted under 35 U.S.C. 154(b) by 160 days.

(21) Appl. No.: 18/539,112

(22) Filed: Dec. 13, 2023

(65) Prior Publication Data

US 2024/0108907 A1     Apr. 4, 2024

Related U.S. Application Data

(63) Continuation of application No. 17/215,782, filed on Mar. 29, 2021, now Pat. No. 11,865,351, which is a
(Continued)

(51) Int. Cl.
*A61N 1/39*          (2006.01)
*A61B 5/00*          (2006.01)
(Continued)

(52) U.S. Cl.
CPC .......... *A61N 1/3904* (2017.08); *A61B 5/0205* (2013.01); *A61B 5/282* (2021.01);
(Continued)

(58) Field of Classification Search
CPC .............................. A61N 1/3904; A61B 5/304
(Continued)

(56) References Cited

U.S. PATENT DOCUMENTS 3,724,455 A     4/1973   Unger
4,583,524 A     4/1986   Hutchins
(Continued)

FOREIGN PATENT DOCUMENTS

WO          WO9839061 A2      9/1998

OTHER PUBLICATIONS

Heartstart MRx and XL AED Algorithm—Application Note, Jul. 2001, Edition 2 Philips Healthcare, USA, 10 pages.
(Continued)

*Primary Examiner* — Nicole F Johnson
(74) *Attorney, Agent, or Firm* — Lee & Hayes, P.C.

(57)          ABSTRACT

A wearable cardioverter defibrillator system includes a support structure that a patient can wear. The system also includes electrodes that contact the patient, and define two or more channels from which ECG signals are sensed. A processor may evaluate the channels by analyzing their respective ECG signals, to determine which contains less noise than the other(s). The analysis can be by extracting statistics from the ECG signals, optionally after first processing them, and then by comparing these statistics. These statistics may include tall peak counts, amplitudes of peaks compared to historical peak amplitudes, signal baseline shift, dwell time near a baseline, narrow peak counts, zero crossings counts, determined heart rates, and so on. Once the less noisy signal is identified, its channel can be followed preferentially or to the exclusion of other channels, for continuing monitoring and/or determining whether to shock the patient.

20 Claims, 18 Drawing Sheets

SAMPLE COMPONENTS OF WEARABLE
CARDIOVERTER DEFIBRILLATOR (WCD)
SYSTEM

Related U.S. Application Data continuation of application No. 15/902,024, filed on Feb. 22, 2018, now Pat. No. 10,960,220.

(60) Provisional application No. 62/472,514, filed on Mar. 16, 2017.

(51) Int. Cl.

| | |
|---|---|
| *A61B 5/0205* | (2006.01) |
| *A61B 5/282* | (2021.01) |
| *A61B 5/304* | (2021.01) |
| *A61B 5/308* | (2021.01) |
| *A61N 1/04* | (2006.01) |

(52) U.S. Cl.
CPC .............. *A61B 5/304* (2021.01); *A61B 5/308* (2021.01); *A61B 5/7221* (2013.01); *A61N 1/046* (2013.01); *A61N 1/3937* (2013.01); *A61N 1/3987* (2013.01)

(58) Field of Classification Search
USPC ............................................................ 607/7
See application file for complete search history.

(56) References Cited

U.S. PATENT DOCUMENTS

| | | | |
|---|---|---|---|
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Bornn |
| RE34,800 | E | 11/1994 | Hutchins |
| 5,394,892 | A | 3/1995 | Kenny et al. |
| 5,405,362 | A | 4/1995 | Kramer et al. |
| 5,474,574 | A | 12/1995 | Payne et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,246,907 | B1 | 6/2001 | Lin et al. |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder et al. |
| 6,427,083 | B1 | 7/2002 | Owen et al. |
| 6,529,875 | B1 | 3/2003 | Nakajima et al. |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,024,037 | B2 | 9/2011 | Kumar |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,548,557 | B2 | 10/2013 | Garstka et al. |
| 8,615,295 | B2 | 12/2013 | Savage et al. |
| 8,644,925 | B2 | 2/2014 | Volpe et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,089,685 | B2 | 7/2015 | Sullivan et al. |
| 9,131,901 | B2 | 9/2015 | Volpe et al. |
| 9,132,267 | B2 | 9/2015 | Kaib |
| 9,408,548 | B2 | 8/2016 | Volpe et al. |
| 9,454,219 | B2 | 9/2016 | Volpe et al. |
| 9,592,403 | B2 | 3/2017 | Sullivan |
| 9,757,581 | B2 | 9/2017 | Sullivan et al. |
| 2002/0161407 | A1 | 10/2002 | Walcott et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2005/0256415 | A1* | 11/2005 | Tan ........................ A61B 5/363 607/9 |
| 2006/0259089 | A1 | 11/2006 | Kim et al. |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0025131 | A1 | 1/2014 | Sullivan et al. |
| 2014/0043149 | A1 | 2/2014 | Cowan et al. |
| 2014/0070957 | A1 | 3/2014 | Longinotti-Buitoni et al. |
| 2014/0085081 | A1 | 3/2014 | Brown et al. |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0283390 | A1 | 10/2015 | Sullivan et al. |
| 2015/0328472 | A1 | 11/2015 | Sullivan et al. |
| 2016/0004831 | A1 | 1/2016 | Carlson et al. |
| 2016/0067514 | A1 | 3/2016 | Sullivan |
| 2016/0082277 | A1 | 3/2016 | Foshee, Jr. et al. |
| 2016/0220832 | A1* | 8/2016 | Sullivan .............. A61N 1/3904 |
| 2017/0056682 | A1 | 3/2017 | Kumar et al. |

OTHER PUBLICATIONS

Klein, et al., "Risk Stratification for Implantable Cardioverter Defibrillator Therapy: the Role of the Wearable Cardioverter-Defibrillator, Clinical update," European Heart Journal, May 31, 2013, pp. 1-14, :loi:10.1093/eurheartj/eht167, European Society of Cardiology.

LifeVest Model 4000, Patient Manual, ZOLL, 2009, PN 2080047 Rev B, 108 pages.

Lifecor LifeVest System Model WCD 3100 Operator's Manual, 2006, PN 2080040 Rev FI, Zoll Lifecor Corporation, Pittsburgh, PA, 48 pages.

Office Action for U.S. Appl. No. 17/215,782, mailed on Jan. 20, 2023, Kim, "Medical Device With Enhanced Electrocardiogram Channel Selection", 12 pages.

Office Action for U.S. Appl. No. 17/215,782, mailed on Jun. 30, 2023, Inventor #1 Jaeho Kim, "Medical Device With Enhanced Electrocardiogram Channel Selection," 16 pages.

Office Action for U.S. Appl. No. 15/902,024, mailed on Feb. 28, 2020, Kim, "Wearable Cardioverter Defibrillator (WCD) System Evaluating Its ECG Signals for Noise According to Tall Peak Counts", 8 pages.

(56)     References Cited

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, pp. 2065-2071.
The LifeVest Network/Patient Data Management System, Zoll, 2015, 20C0503 Rev A, 4 pages.

* cited by examiner

82

170

104    85

180
OUTSIDE
MONITORING
DEVICE

111

105

108

100
EXTERNAL
DEFIBRILLATOR

*SAMPLE COMPONENTS OF WEARABLE*
*CARDIOVERTER DEFIBRILLATOR (WCD)*
*SYSTEM*

SAMPLE COMPONENTS OF EXTERNAL DEFIBRILLATOR

ELECTRODES & ECG SIGNALS
ALONG MULTIPLE VECTORS

IDEALIZED, NOISE-FREE ECG SIGNAL
FROM SINGLE CHANNEL

700

710   SENSE ECG SIGNALS FROM DIFFERENT CHANNELS

740   COUNT PEAKS OF ECG SIGNALS WITH AMPLITUDES LARGER THAN THRESHOLD

750   EVALUATE THAT ONE ECG CHANNEL IS PREFERRED OVER OTHER(S)

760   SENSE & ANALYZE THIRD ECG SIGNAL FROM PREFERRED CHANNEL(S)

770   SENSE FOURTH ECG SIGNAL OF PATIENT

780
FROM 4TH ECG SIGNAL,
SHOCK CRITERION
MET?

NO

YES

790   DELIVER SHOCK TO THE PATIENT

_METHODS_

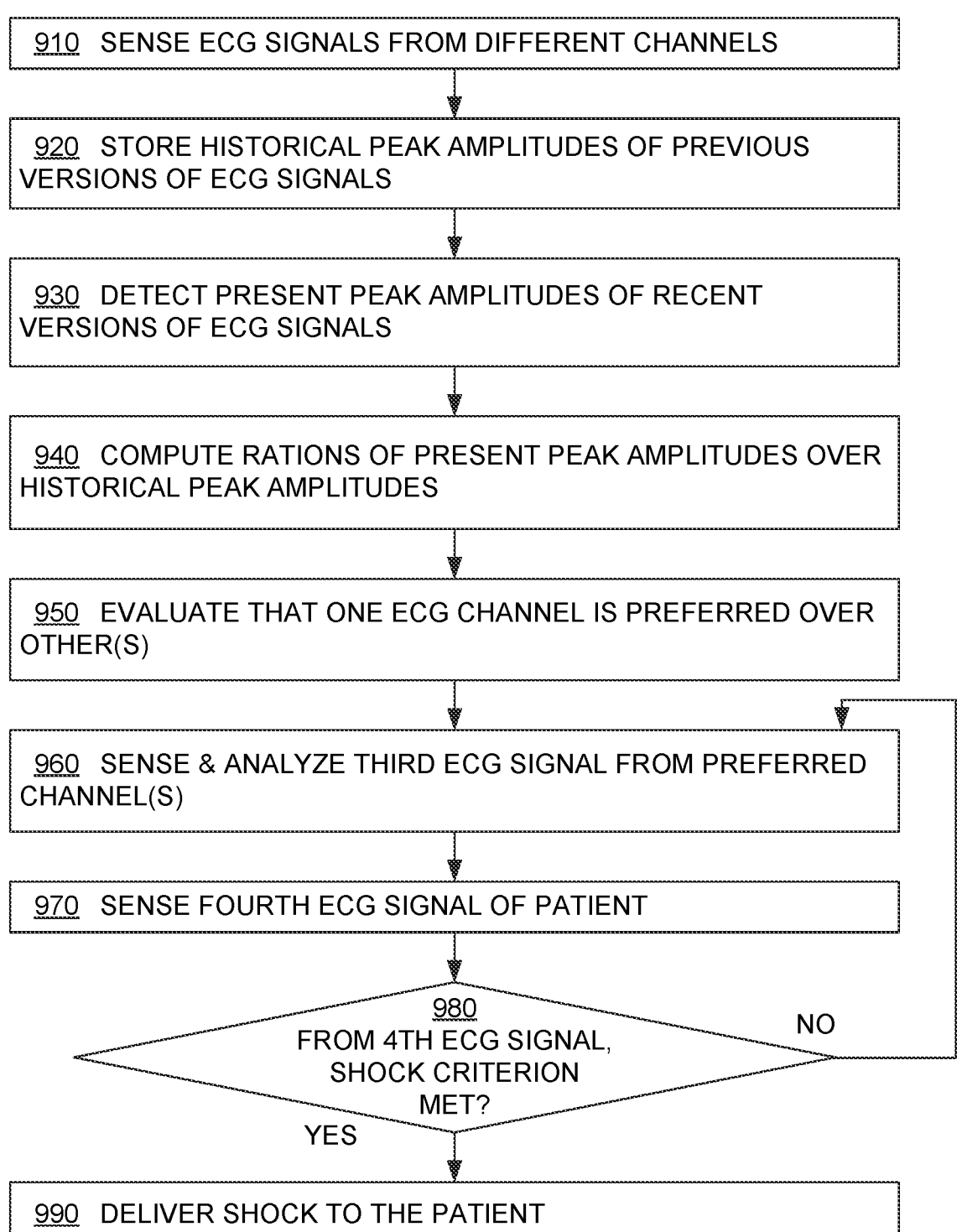

900

910   SENSE ECG SIGNALS FROM DIFFERENT CHANNELS

920   STORE HISTORICAL PEAK AMPLITUDES OF PREVIOUS VERSIONS OF ECG SIGNALS

930   DETECT PRESENT PEAK AMPLITUDES OF RECENT VERSIONS OF ECG SIGNALS

940   COMPUTE RATIONS OF PRESENT PEAK AMPLITUDES OVER HISTORICAL PEAK AMPLITUDES

950   EVALUATE THAT ONE ECG CHANNEL IS PREFERRED OVER OTHER(S)

960   SENSE & ANALYZE THIRD ECG SIGNAL FROM PREFERRED CHANNEL(S)

970   SENSE FOURTH ECG SIGNAL OF PATIENT

980 FROM 4TH ECG SIGNAL, SHOCK CRITERION MET?          NO

YES

990   DELIVER SHOCK TO THE PATIENT

FIG. 9                                    *METHODS*

1100

1110    SENSE ECG SIGNALS FROM DIFFERENT CHANNELS

1120    IDENTIFY BASELINES OF ECG SIGNALS

1140    DETECT BASELINE SHIFTS OF ECG SIGNALS

1150    EVALUATE THAT ONE ECG CHANNEL IS PREFERRED OVER OTHER(S)

1160    SENSE & ANALYZE THIRD ECG SIGNAL FROM PREFERRED CHANNEL(S)

1170    SENSE FOURTH ECG SIGNAL OF PATIENT

1180    FROM 4TH ECG SIGNAL, SHOCK CRITERION MET?    NO

YES

1190    DELIVER SHOCK TO THE PATIENT

FIG. 11        *METHODS*

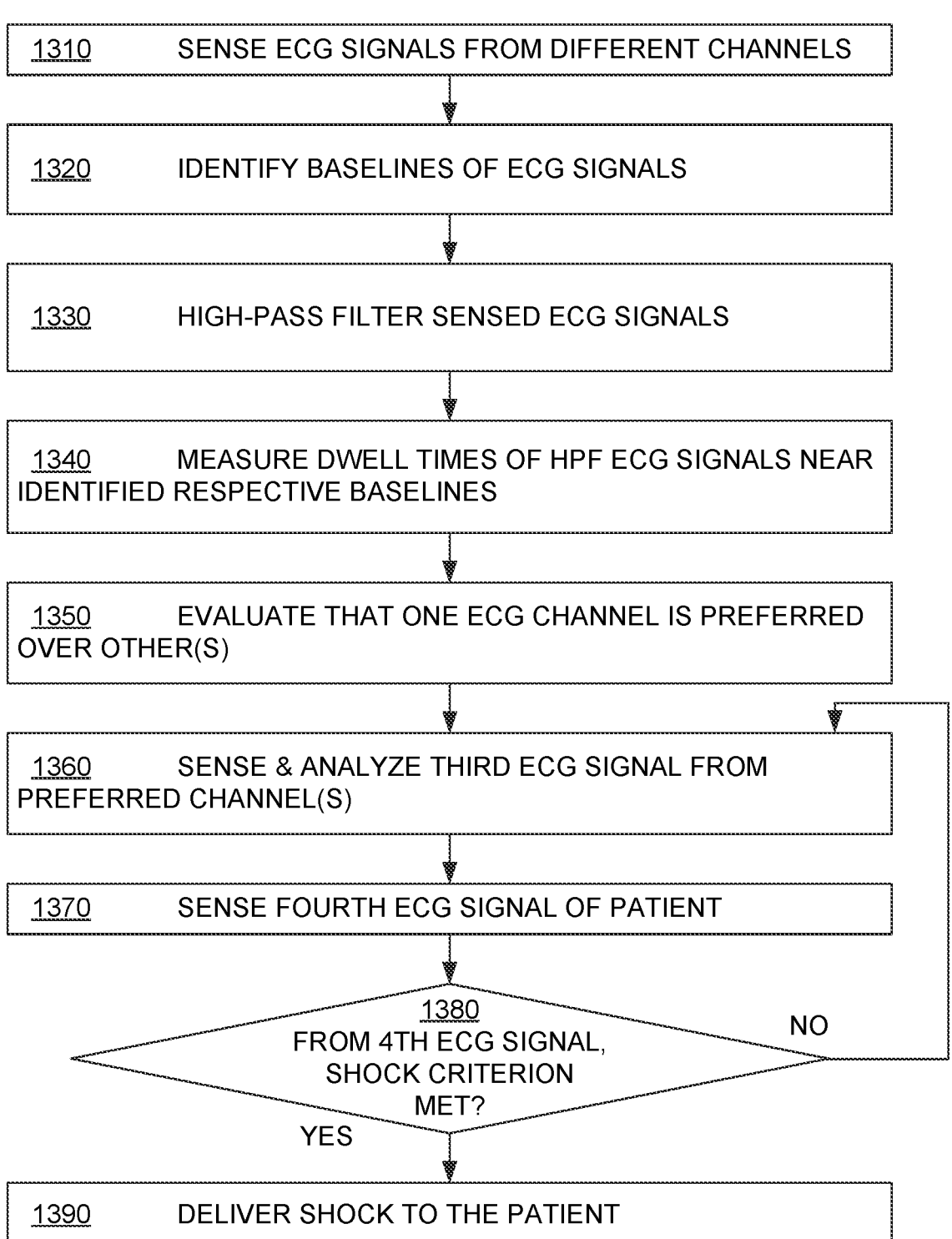

1300

| 1310 | SENSE ECG SIGNALS FROM DIFFERENT CHANNELS |

| 1320 | IDENTIFY BASELINES OF ECG SIGNALS |

| 1330 | HIGH-PASS FILTER SENSED ECG SIGNALS |

| 1340 | MEASURE DWELL TIMES OF HPF ECG SIGNALS NEAR IDENTIFIED RESPECTIVE BASELINES |

| 1350 | EVALUATE THAT ONE ECG CHANNEL IS PREFERRED OVER OTHER(S) |

| 1360 | SENSE & ANALYZE THIRD ECG SIGNAL FROM PREFERRED CHANNEL(S) |

| 1370 | SENSE FOURTH ECG SIGNAL OF PATIENT |

1380
FROM 4TH ECG SIGNAL, SHOCK CRITERION MET?

NO

YES

| 1390 | DELIVER SHOCK TO THE PATIENT |

FIG. 13

*METHODS*

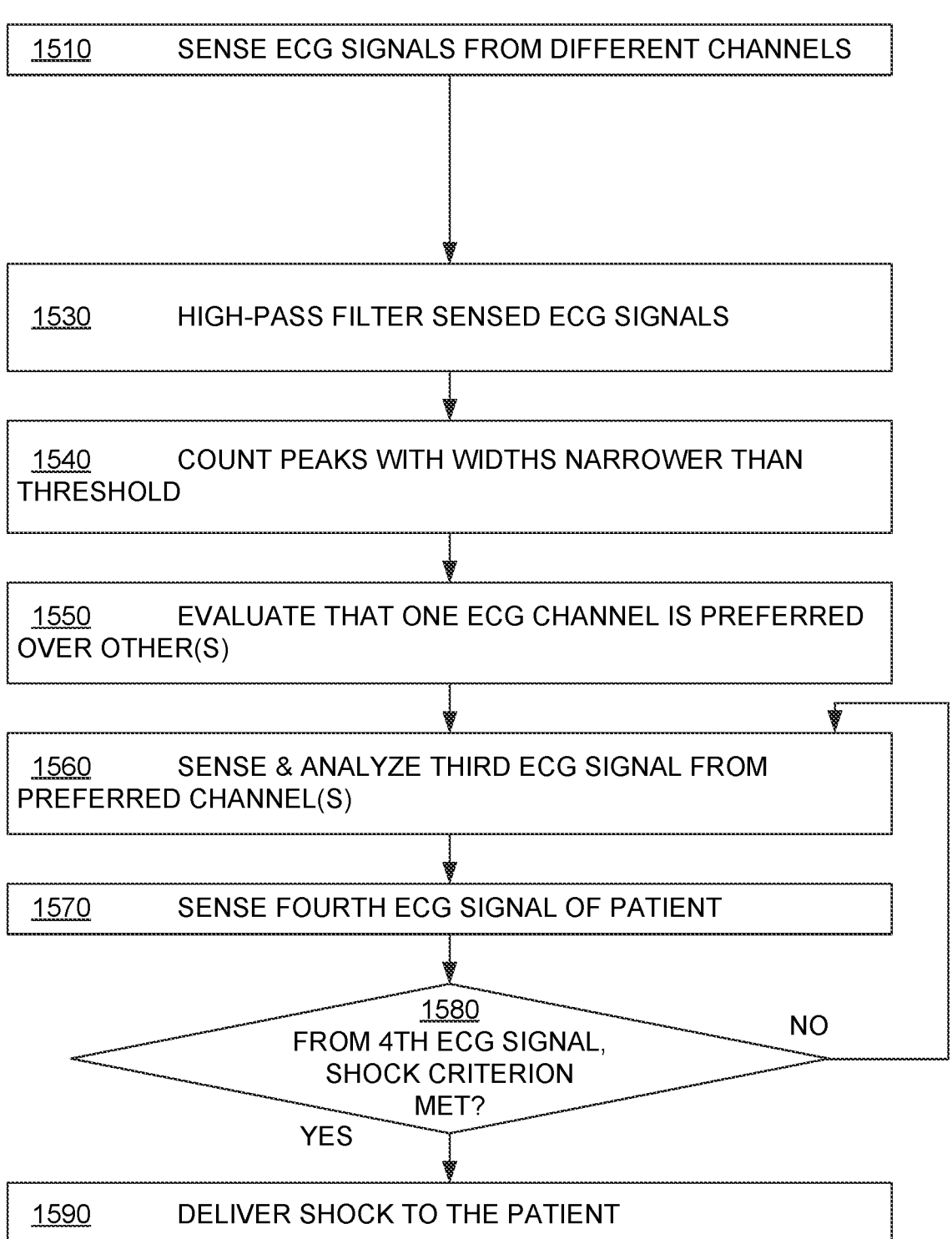

1500

1510     SENSE ECG SIGNALS FROM DIFFERENT CHANNELS

1530     HIGH-PASS FILTER SENSED ECG SIGNALS

1540     COUNT PEAKS WITH WIDTHS NARROWER THAN THRESHOLD

1550     EVALUATE THAT ONE ECG CHANNEL IS PREFERRED OVER OTHER(S)

1560     SENSE & ANALYZE THIRD ECG SIGNAL FROM PREFERRED CHANNEL(S)

1570     SENSE FOURTH ECG SIGNAL OF PATIENT

1580 FROM 4TH ECG SIGNAL, SHOCK CRITERION MET?

NO

YES

1590     DELIVER SHOCK TO THE PATIENT

FIG. 15                          *METHODS*

1700

| 1710 | SENSE ECG SIGNALS FROM DIFFERENT CHANNELS |

| 1730 | HIGH-PASS FILTER SENSED ECG SIGNALS |

| 1740 | COUNT ZERO CROSSINGS OF HPF ECG SIGNALS |

| 1750 | EVALUATE THAT ONE ECG CHANNEL IS PREFERRED OVER OTHER(S) |

| 1760 | SENSE & ANALYZE THIRD ECG SIGNAL FROM PREFERRED CHANNEL(S) |

| 1770 | SENSE FOURTH ECG SIGNAL OF PATIENT |

1780
FROM 4TH ECG SIGNAL,
SHOCK CRITERION
MET?

NO

YES

| 1790 | DELIVER SHOCK TO THE PATIENT |

FIG. 17                    *METHODS*

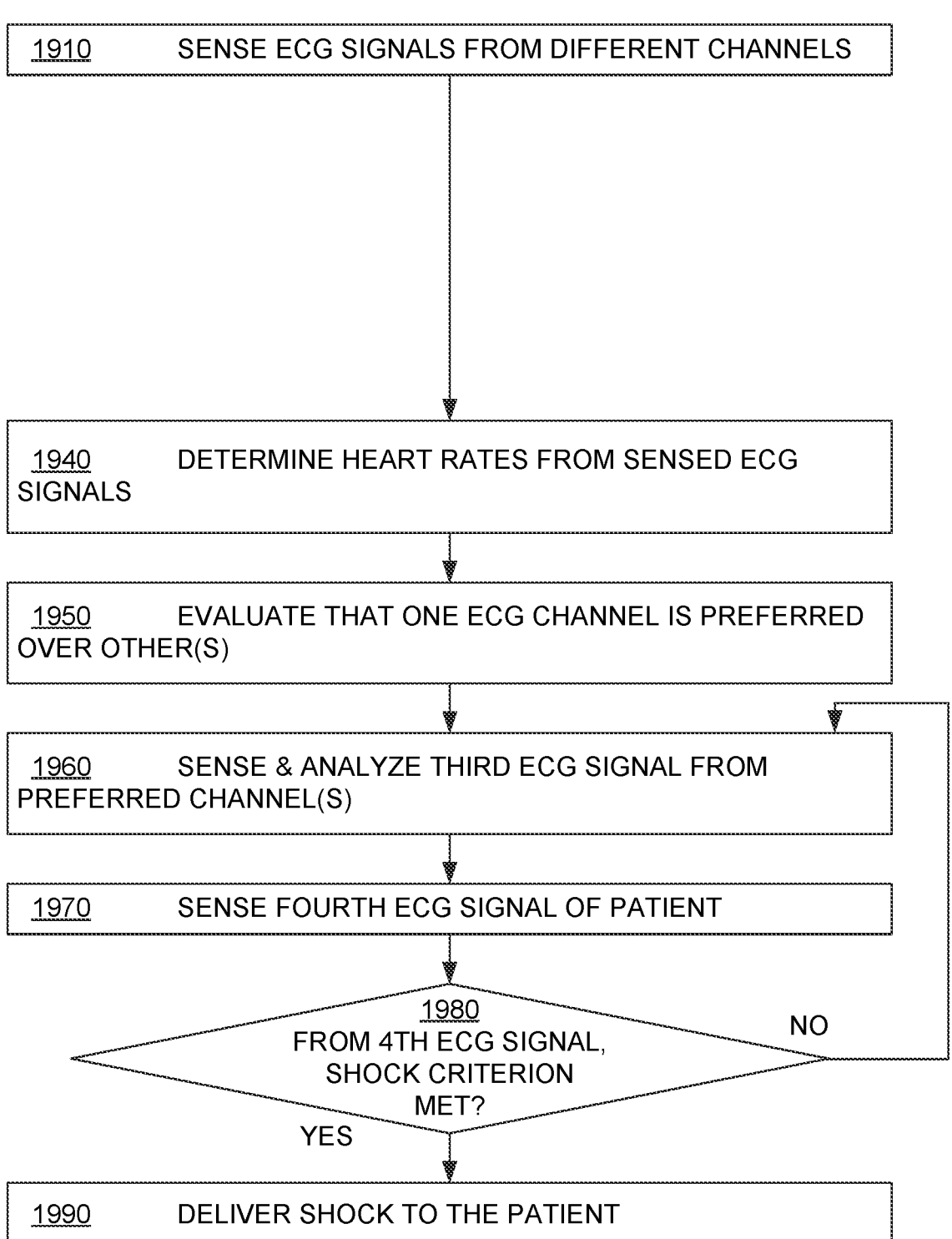
1900
1910    SENSE ECG SIGNALS FROM DIFFERENT CHANNELS
1940    DETERMINE HEART RATES FROM SENSED ECG SIGNALS
1950    EVALUATE THAT ONE ECG CHANNEL IS PREFERRED OVER OTHER(S)
1960    SENSE & ANALYZE THIRD ECG SIGNAL FROM PREFERRED CHANNEL(S)
1970    SENSE FOURTH ECG SIGNAL OF PATIENT
1980
FROM 4TH ECG SIGNAL, SHOCK CRITERION MET?
NO
YES
1990    DELIVER SHOCK TO THE PATIENT
FIG. 19          *METHODS*

MEDICAL DEVICE WITH ENHANCED ELECTROCARDIOGRAM CHANNEL SELECTION

CROSS-REFERENCE TO RELATED APPLICATIONS

This application is a continuation of U.S. patent application Ser. No. 17/215,782, filed on Mar. 29, 2021 and titled "Medical Device With Enhanced Electrocardiogram Channel Selection," which is a continuation of U.S. patent application Ser. No. 15/902,024, filed on Feb. 22, 2018 and titled "Wearable Cardioverter Defibrillator (WCD) System Evaluating its ECG Signals for Noise According to Tall Peak Counts," which claims the benefit of and priority to U.S. Provisional Patent Application Ser. No. 62/472,514 filed on Mar. 16, 2017 entitled "ECG Vector Selection in a Multi-Electrodes Wearable Cardioverter Defibrillator," all of which are incorporated herein by reference in their entirety.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

A challenge in the prior art is that the patient's ECG signal may be corrupted by electrical noise. Such noise on the ECG signal can be generated at the electrode-skin interface, for example due to patient movement.

Noise on the ECG signal can be a significant problem, since the ECG is interpreted for diagnosing the patient who is wearing the WCD system. A noisy ECG signal can cause the WCD system to either attempt to shock the patient when a shock is not needed, or it can cause the WCD system to fail to shock when a shock is needed.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of wearable cardioverter defibrillator (WCD) systems, storage media that store programs, and methods, the use of which may help overcome problems and limitations of the prior art.

In embodiments, a wearable cardioverter defibrillator system includes a support structure that a patient can wear. The system also includes electrodes that contact the patient, and define two or more channels from which ECG signals are sensed. A processor may evaluate the channels by analyzing their respective ECG signals, to determine which contains less noise than the other(s). The analysis can be by extracting statistics from the ECG signals, optionally after first processing them, and then by comparing these statistics. These statistics may include tall peak counts, amplitudes of peaks compared to historical peak amplitudes, signal baseline shift, dwell time near a baseline, narrow peak counts, zero crossings counts, determined heart rates, and so on. Once the less noisy signal is identified, its channel can be followed preferentially or to the exclusion of other channels, for continuing monitoring and/or determining whether to shock the patient.

An advantage can be that the continuing monitoring of the patient may take place from a less noisy ECG signal. This, in turn, may help the WCD system make a better shock/no shock decision.

These and other features and advantages of the claimed invention will become more readily apparent in view of the embodiments described and illustrated in this specification, namely from this written specification and the associated drawings.

BRIEF DESCRIPTION OF THE DRAWINGS

FIG. 9 is a flowchart for illustrating methods according to embodiments.

FIG. 13 is a flowchart for illustrating methods according to embodiments.

FIG. 15 is a flowchart for illustrating methods according to embodiments.

FIG. 19 is a flowchart for illustrating methods according to embodiments.

DETAILED DESCRIPTION

As has been mentioned, the present description is about wearable cardioverter defibrillator (WCD) systems, and related storage media, programs and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
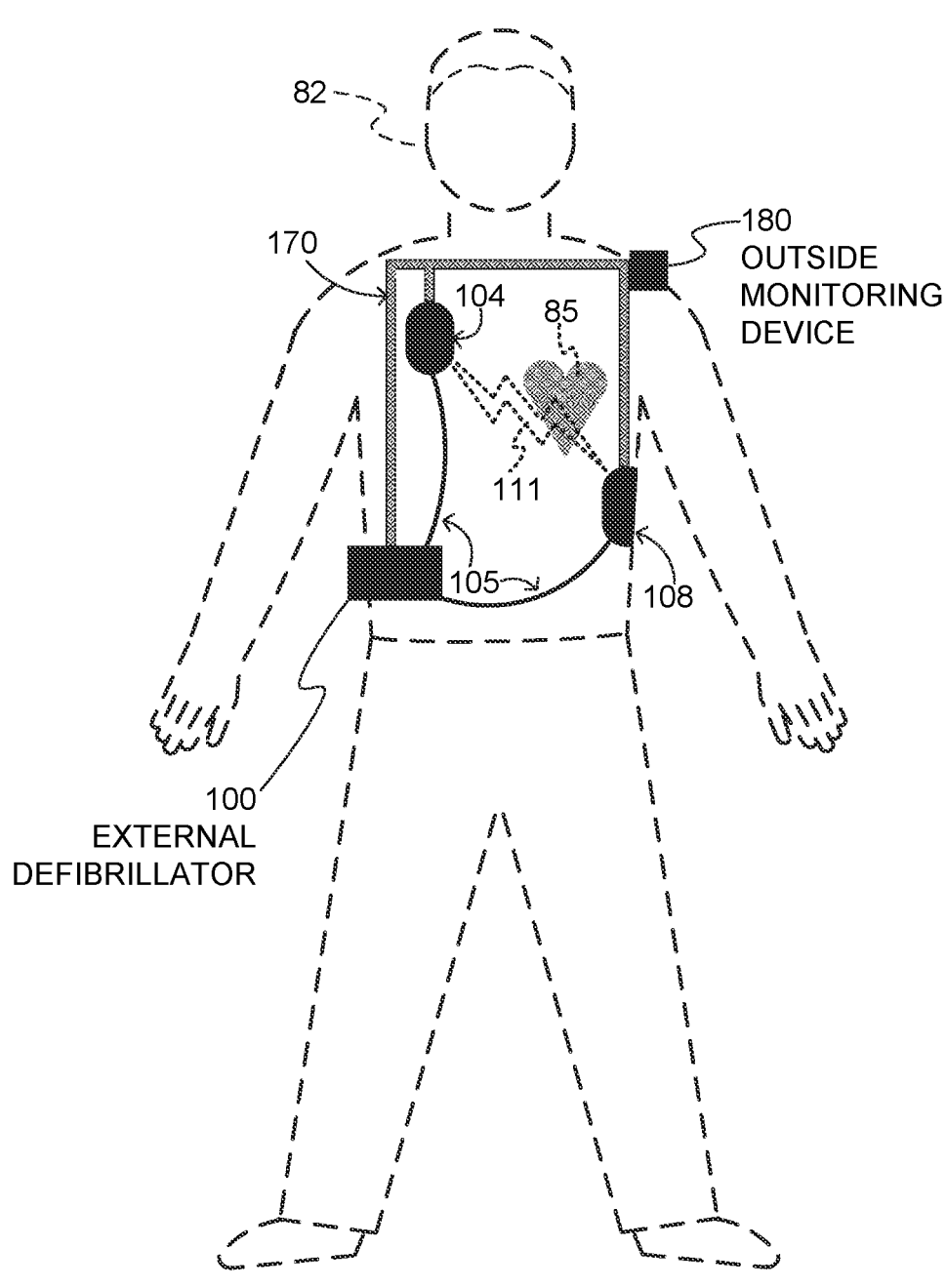
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bedridden.

FIG. 1 also depicts components of a WCD system made according to embodiments.

One such component is a support structure 170 that is wearable by. patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
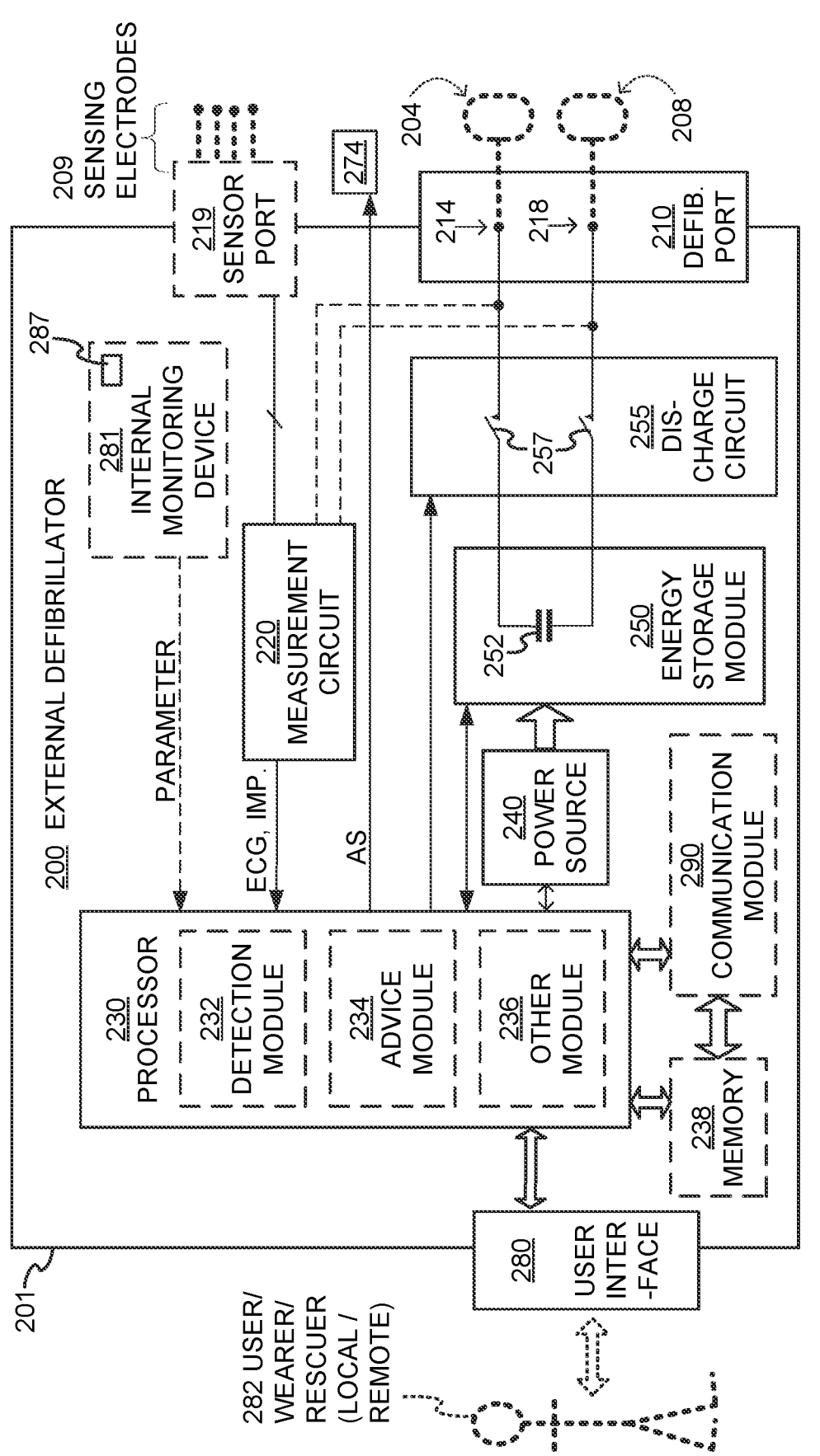
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physic-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

Figure 3:
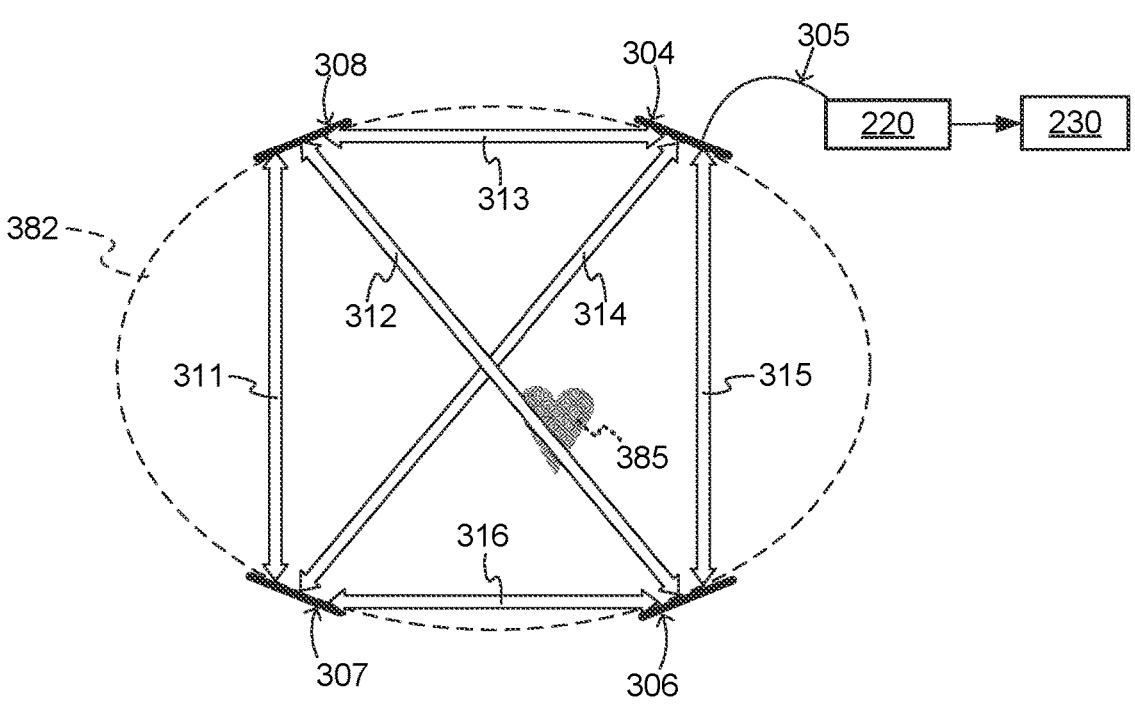
FIG. 3 is a conceptual diagram for illustrating an example of how different electrodes may capture ECG signals along different vectors according to embodiments.

FIG. 3 is a conceptual diagram for illustrating how electrodes of a WCD system may sense or capture ECG signals along different vectors according to embodiments. A section of a patient 382 having a heart 385 is shown. There are four electrodes 304, 306, 307, 308, attached to the torso of patient 382. Each of these four electrodes 304, 306, 307, 308 can have a wire lead. A sample such wire lead 305 is shown that leads to a measurement circuit 220, and from there to a processor 230, both of which are described in more detail later in this document.

Any pair of these electrodes 304, 306, 307, 308 may define a vector across with an ECG signal may be measured. These vectors are also known as channels and ECG channels. The four electrodes 304, 306, 307, 308 therefore can define six channels, or vectors, across which six respective ECG signals 311, 312, 313, 314, 315, 316 can be sensed. FIG. 3 thus illustrates a multi-vector situation. In FIG. 3 it will be understood that electrodes 304, 306, 307, 308 are drawn on the same plane for simplicity, while that is not necessarily always the case. Accordingly, the vectors of ECG signals 311, 312, 313, 314, 315, 316 are not necessarily on the same plane, either. Of course it will be appreciated that any electrodes of the WCD system that are used only for defibrillation and not for sensing ECG do not define such ECG channels.

Any one of ECG signals 311, 312, 313, 314, 315, 316 might provide sufficient data for making a shock/no shock determination. The effort is to shock when needed, and not shock when not needed. The problem is that, at any given point in time, some of these ECG signals may include noise, while others not. The noise may be due to patient movement or how well the electrodes contact the skin. The noise problem for a WCD system may be further exacerbated by the desire to use dry, non-adhesive monitoring electrodes. Dry, non-adhesive electrodes are thought to be more comfortable for the patient to wear in the long term, but may produce more noise than a conventional ECG monitoring electrode that includes adhesive to hold the electrode in place and an electrolyte gel to reduce the impedance of the electrode-skin interface.

Returning to FIG. 2, defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the physiological input reflects an ECG measurement. The patient parameter can be an ECG, which can be sensed as a voltage difference between electrodes 204, 208. In addition the patient parameter can be an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are sensed or captured according to embodiments, and determining whether a shock criterion is met. The determination can be made from a rhythm analysis of the sensed or captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

The impact of noise on the ECG signal is now described in terms of its effect on an idealized ECG signal.

Figure 4:
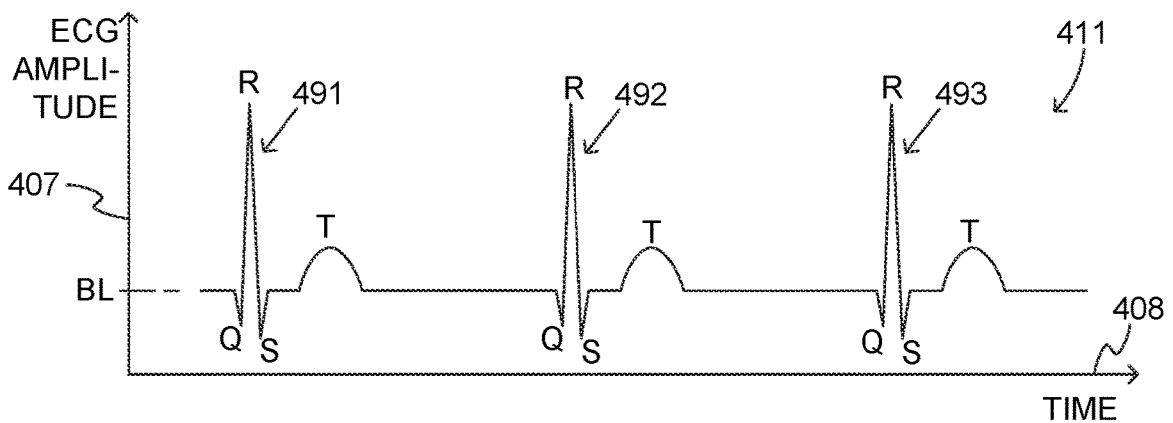
FIG. 4 shows a time diagram of an idealized, noise-free ECG signal in the prior art, as it might be received from a single ECG channel.

FIG. 4 shows a time diagram 411. Diagram 411 has an ECG amplitude axis 407 and a time axis 408. Diagram 411 depicts a somewhat-idealized, noise-free ECG signal of patient 82, as it might be sensed from a single channel 311. The ECG signal of diagram 411 hovers around a baseline that has a value BL. Value BL is often not zero, as an ECG signal usually has a DC offset. The baseline in diagram 411 is shown as horizontal, although in some instances it changes due to noise, as described later in this document.

The ECG signal of diagram 411 includes three full heartbeats. In particular, three peaks 491, 492, 493 are shown, which occur sequentially. It will be recognized that peaks 491, 492, 493 are due to QRS complexes, each of which is followed by a T-wave of lesser amplitude. In this somewhat-idealized signal, a P-wave before each QRS complex and a U-wave after each T-wave are not shown at all. The time durations between successive peaks 491, 492, 493 are typically used for detecting the heart rate, because their large amplitude relative to the remainder of the ECG signal makes them easier to identify and/or detect. This remains true especially while peaks from noise are shorter than QRS peaks.

FIG. 4 was presented as a reference. A more-real-life example is now described, where noise is present in ECG signals obtained from different ECG channels.

Figure 5:
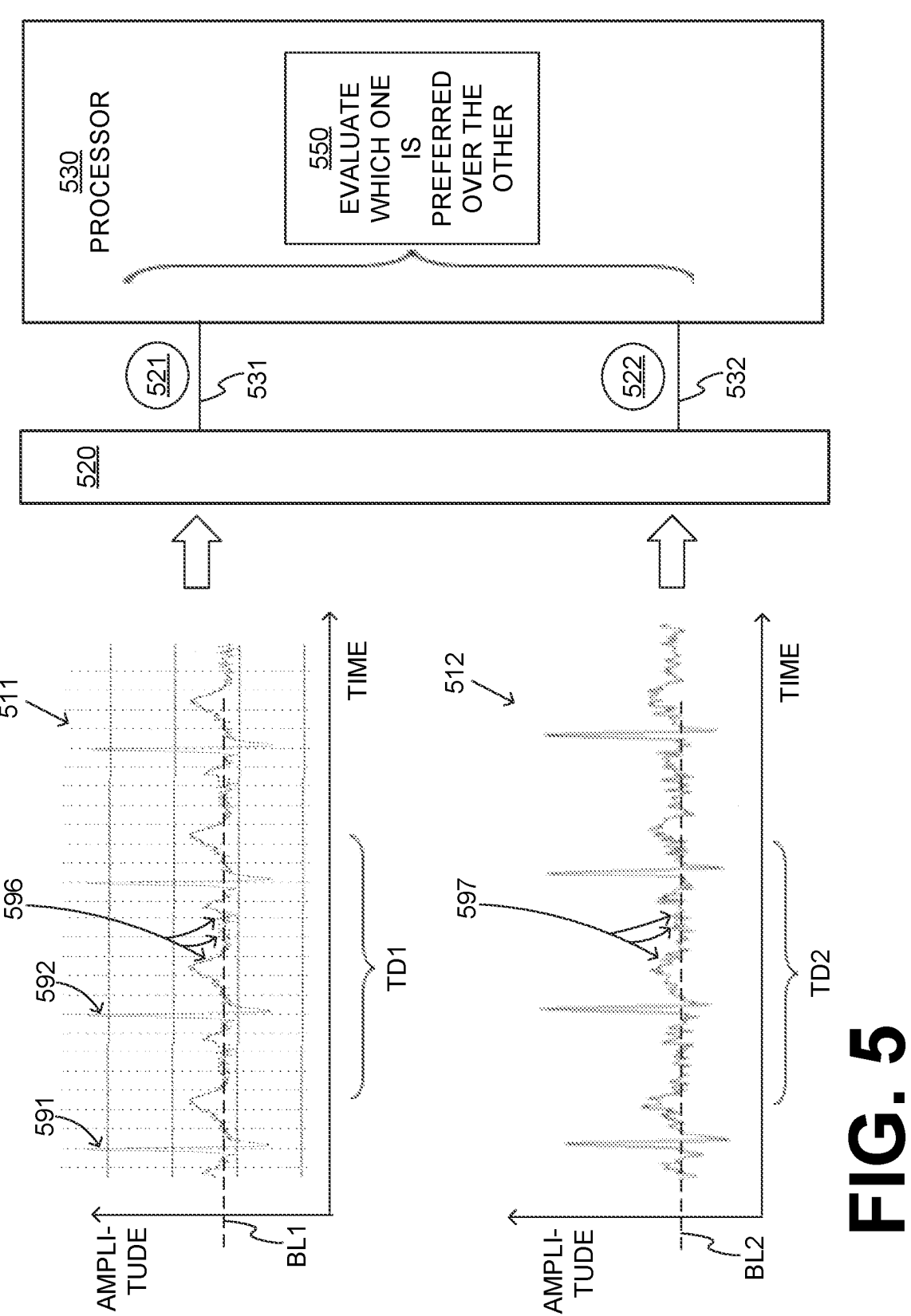
FIG. 5 is a composite diagram illustrating that different possible ECG signals can be available from different ECG channels, and an evaluation operation can indicate which one of these channels is preferred over the other for continuing monitoring and/or for arriving at a shock/no shock determination according to embodiments.

FIG. 5 is a composite diagram. On the left-hand side are time diagrams 511, 512 of ECG signals that may be received from different channels. These ECG signals hover around baselines BL1, BL2. These ECG signals further include peaks due to QRS complexes as described above, for example the ECG signal of diagram 511 includes QRS peaks 591, 592, etc. Time durations TD1, TD2 on the horizontal time axes can be considered, for selecting portions of the ECG signals to enable meaningful comparisons. For example, time durations TD1, TD2 can be chosen to be equal, coincident and so on. In addition, it may be considered whether to make these time durations long, short, fragmented and so on.

In addition, these ECG signals of time diagrams 511, 512 contain noise, as their lines are largely jagged. Where the idealized ECG signal of FIG. 4 had smooth lines, noise manifests in the ECG signals of FIG. 5 as multiple small peaks 596, 597. In this example, peaks 596, 597 from noise have less amplitude compared to the peaks due to the QRS complexes, but that is not always the case.

FIG. 5 also shows a measurement circuit 520, which can be made as described for measurement circuit 220. In other words, measurement circuit 520 can be configured to sense a first ECG signal and a second ECG signal from respectively a first one and a second one of the channels that are defined by the electrodes. In fact, measurement circuit 520 can be configured to sense as many channels are available, namely 3, 6, etc.

On the right-hand side, FIG. 5 also shows a processor 530, which can be made as described processor 230. Measurement circuit 520 may render ECG signals 521, 522 to processor 530 over conductors 531, 532. ECG signals 521, 522 have been created responsive to the ECG signals of diagrams 511, 512. Measurement circuit 520 includes circuitry for sampling the ECG signals, although that is not required. Measurement circuit 520 may also include analog to digital converter(s) (ADCs) for converting the ECG signals to numerical values, although that is not required. In the latter case, ECG signals 521, 522 can be just numbers whose time coordinates are the ordinal numbers of samples, and conductors 531, 532 can be data pathways within processor 530.

Processor 530 may further perform an operation 550. According to operation 550, statistics may be extracted from the ECG signals, optionally after first processing them. There are many possible statistics according to embodiments that are described later in this document in more detail. Any one of these statistics may be extracted. Some of these statistics are indicative of a signal-to-noise ratio (SNR) for the channel's signal.

In some embodiments, a combination of statistics may be extracted. If a combination, the statistics can optionally be aggregated into a single number, for example by using weighting coefficients, and so on.

Then, processor 530 may evaluate that one of the channels is preferred over the other channel, responsive to comparing the extracted statistics of the respective ECG signals of the channels. For example, if the second one of the ECG signals has superior statistics over the first one of the ECG signals, then the evaluation is that the second channel is preferred over the first channel.

And, in embodiments, what was described for comparing two channels can be implemented also for more than two channels. For example, where the electrodes define at least three channels, measurement circuit 520 can be configured to sense at least three distinct ECG signals from the at least three channels, and evaluate between two of the three signals, or among all three, and so on.

Alternately, multiple statistics may be used sequentially, a first one to select some almost-equally performing channels, a second one to narrow down among them and so on. For example, once the ECG vectors with the best statistics are identified, other ECG vectors with similar statistics can be also selected. These ECG vectors can be used collectively, or another selection criterion can be applied to reduce the selected ECG vectors. For instance, when multiple ECG vectors show a similar heart rate, the ECG vector with the larger QRS amplitude may be preferred. Or, the ECG vector with the less number of narrow spikes may be preferred. Or, the ECG vector with the higher percentage of the filtered signal near the baseline may be preferred.

It should be understood that more than one ECG vector might be selected. For example, if multiple ECG vectors meet the selection criteria, it might be better to perform rhythm analysis on multiple ECG vectors rather than just one.

The one or more preferred channels can be used preferentially over the other channel(s), for continuing monitoring and/or for arriving at a shock/no shock determination according to embodiments. For example, a third ECG signal can be sensed from the preferred channel and not from the other channel, subsequently to sensing the first and the second ECG signal. Processor 530 may then determine, from a fourth further subsequently sensed ECG signal, whether or not a shock criterion is met. Responsive to the shock criterion being met, discharge circuit 255 can be controlled to discharge the stored electrical charge. The fourth ECG signal may have been sensed from any channel. In some embodiments, the fourth ECG signal has been sensed from the preferred channel and not from the other channel.

It should be further recognized that, while a certain channel is preferred at a certain time, the preference may change at a later time. This may be due to the patient moving, changing their position, their activity, and so on. In embodiments, the processes for extracting statistics and evaluating the statistics are repeated occasionally, or responsive to sudden changes in inputs from possibly other sensors of the WCD system, and so on.

In some embodiments, memory 238 can be configured to store a portion of the ECG signal that has been sensed from the preferred ECG channel. Such portions could be, for example, defined by time durations TD1, TD2. In such embodiments, it can be determined whether or not a shock criterion is met from the stored portion of the ECG signal. In fact, it could be determined whether or not the shock criterion is met from the stored portion of the ECG signal, and not at all from the other, non-preferred ECG signal.

Figure 6:
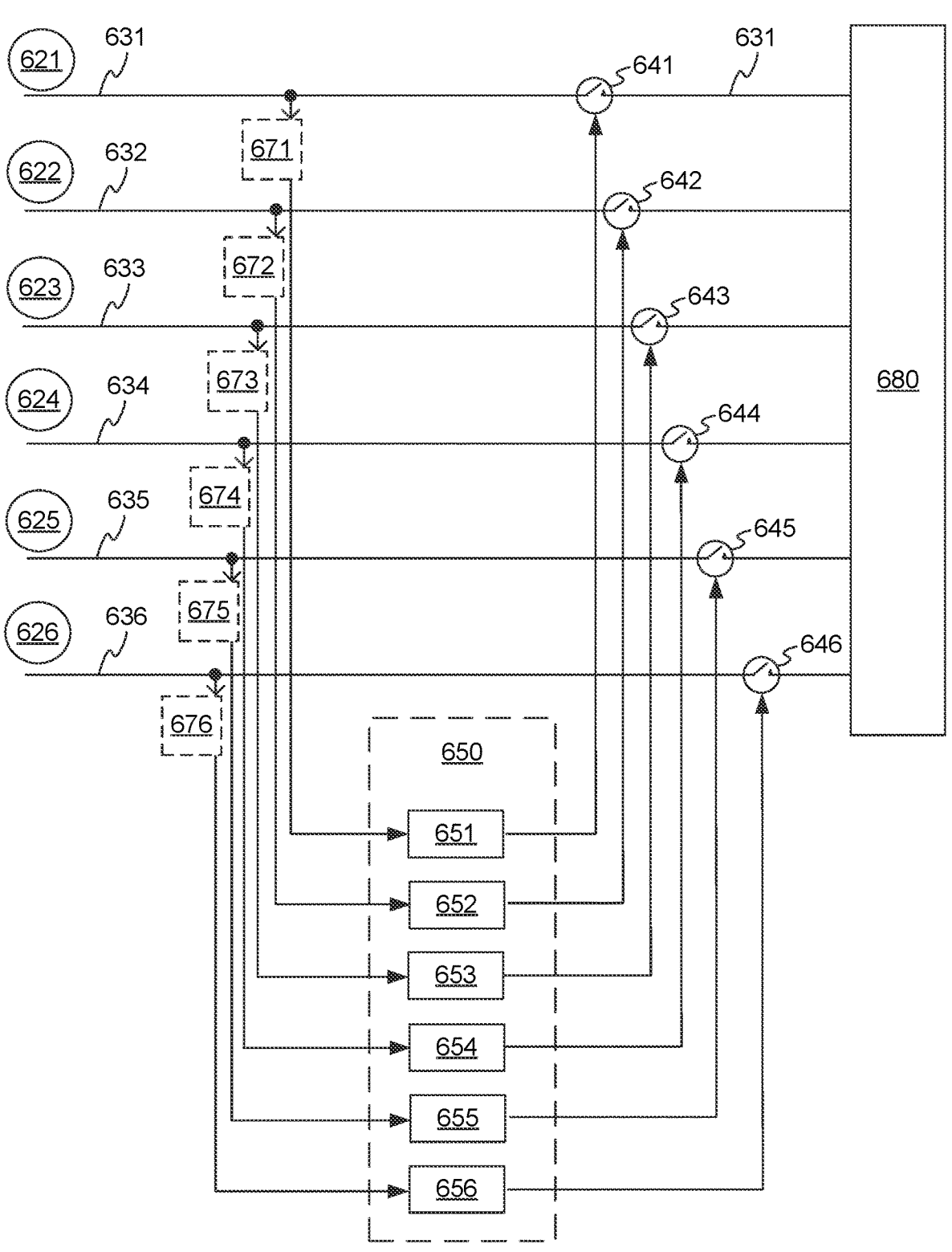
FIG. 6 is a block diagram of a sample arrangement of components according to embodiments, where different channels are evaluated according to their ECG signals, and the evaluation is used to control which channel's ECG signal is used for continuing monitoring and/or for arriving at a shock/no shock determination.

FIG. 6 is a block diagram of a sample arrangement of components according to embodiments, while there can be other arrangements. The diagram of FIG. 6 can be for a WCD system with six channels. Systems with other numbers of channels can be accommodated by suitable modifications.

In FIG. 6, conductors 631, 632, 633, 634, 635, 636 can be as described for conductors 531, 532. Conductors 631-636 can receive ECG signals 621, 622, 623, 624, 625, 626, which can be as described for ECG signals 521, 522. Conductors 631-636 can conduct ECG signals 621-626 to a further block 680, if permitted by respective switches 641, 642, 643, 644, 645, 646. In fact, conductor 631 is indicated as such before and after switch 641. Block 680 can be a block of further processing, such as for analyzing the received ECG signal to monitor the patient. In some embodiments, block 680 is advice module 234.

In embodiments, switches 641-646 can be controlled to allow the preferred one(s) of ECG signals 621-626 to reach block 680, while not allowing the non-preferred, other ECG signals to reach block 680. In some embodiments only one of the channels is preferred. In other embodiments, two or more channels are received and both their signals can be used. In some instances these signals can be combined, for example as described in U.S. Pat. No. 9,757,581.

In embodiments, switches 641-646 can be controlled respectively from circuits 651, 652, 653, 654, 655, 656. In turn, these circuits 651-656 may also receive ECG signals

621-626 by tapping into conductors 631-636 as shown. Circuits 651-656 can be considered as an aggregate block 650 that performs noise evaluation on ECG signals 621-626. Block 650 may be the part of processor 530 that performs operation 550.

ECG signals 621-626 that are thus received for noise evaluation may be stored in optional memories 671, 672, 673, 674, 675, 676. Such storing permits operations like looking at a signal also backwards in time, and so on, which can be useful for some of the individual operations described below.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described. These methods may be performed by WCD systems; operations of these methods may be caused to be performed by processors of WCD systems, and so on, as also described elsewhere in this document.

Figure 7:
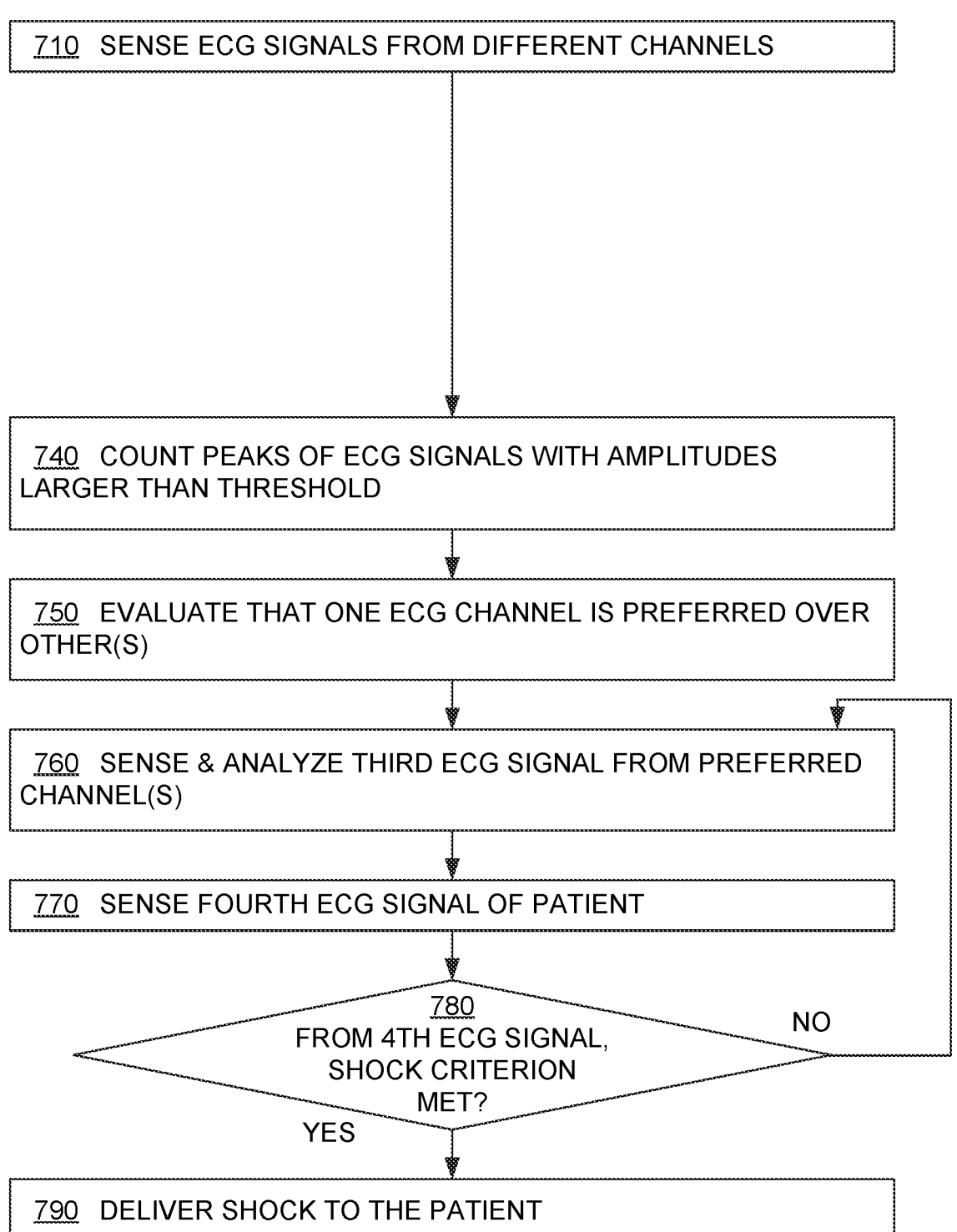
FIG. 7 is a flowchart for illustrating methods according to embodiments.

FIG. 7 shows a flowchart 700 for describing methods according to embodiments.

According to an operation 710, ECG signals from different channels may be sensed by the measurement circuit. For example a first ECG signal and a second ECG signal may be sensed from respectively a first one and a second one of the available channels.

According to another operation 740, peaks of the ECG signals sensed at operation 710 may be counted. These counted peaks may be those occurring over respective time durations, and have amplitudes larger than a threshold. These can also be thought of as tall peaks. It will be appreciated that these counted tall peaks amount to one embodiment of the aforementioned statistics that can be extracted from the ECG signals. An example of performing this operation is now described.

Figure 8:
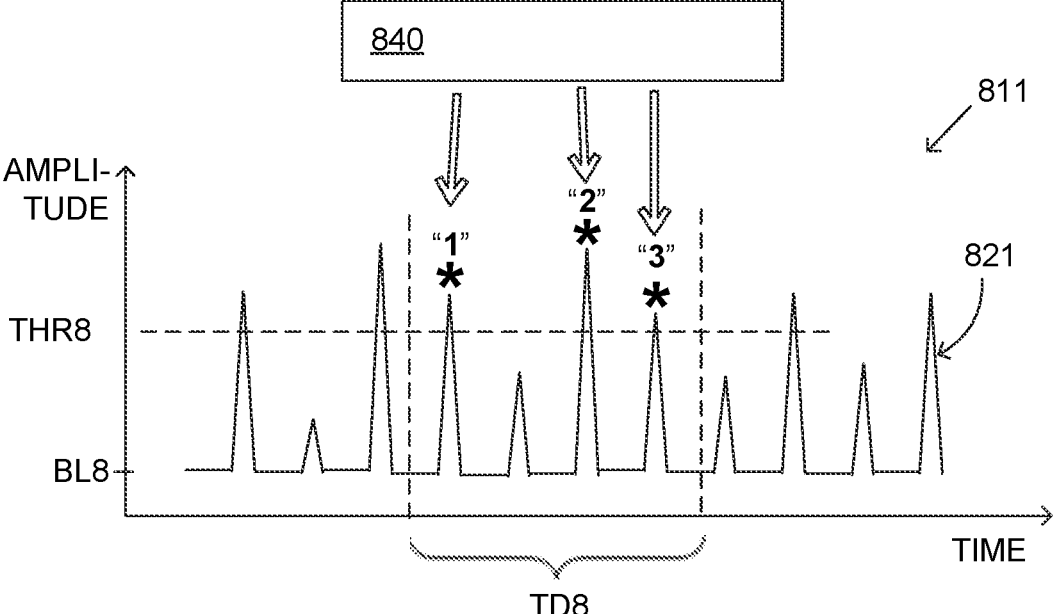
FIG. 8 is a time diagram of a sample ECG signal whose channel is being evaluated according to embodiments of FIG. 7.

Referring now to FIG. 8, a time diagram 811 is shown. Diagram 811 depicts a somewhat-simplified ECG signal 821, which may be the first or the second ECG signal whose channel is being evaluated. The simplification is that only peaks are shown, while all other features are shown zeroed-out at a baseline BL8.

An operation 840 is also depicted, which could be as operation 740. According to operation 840, peaks can be counted that occur over time duration TD8 and have amplitudes larger than a threshold THR8. In this instance, three peaks "1", "2", "3" shown by asterisks are counted, and the total peak count is 3.

Returning now to FIG. 7, according to another operation 750, it may be evaluated that one of the ECG channels is preferred over the other, for example responsive to the statistics of operation 740. For instance, it may be evaluated that one of the first channel and the second channel is preferred over the other, responsive to one of the first ECG signal and the second ECG signal having fewer of the counted peaks than the other. In some embodiments, the one of the two channels whose ECG signal has the fewer counted peaks, of the type seen in FIG. 8, is the preferred channel.

According to another operation 760, a third ECG signal of the patient may be sensed, subsequently to sensing the first and the second ECG signal. The third ECG signal may be sensed from the preferred channel, and not from the other channel, for continuing to monitor the patient. The preferred channel of the two may have been established as per operation 750. The third ECG signal may be then analyzed.

According to another operation 770, a fourth ECG signal of the patient may be sensed, subsequently to the third ECG signal of operation 760. According to another operation 780, it may be determined, from the fourth ECG signal, whether or not a shock criterion is met.

If at operation 780 the answer is no, then execution may go to another operation. For example, execution may return to a previous operation, such as operation 760. Execution may even return to operation 740, so as to search for perhaps a different preferred channel, in the event that noise conditions have changed among the channels.

If at operation 780 the answer is yes then, according to another operation 790, a shock may be delivered to the patient. For instance, responsive to the shock criterion of operation 780 being met, the discharge circuit may be controlled to discharge the electrical charge stored in the energy storage module, while the support structure is worn by the patient, so as to cause a shock to be delivered to the ambulatory patient.

FIG. 9 shows a flowchart 900 for describing methods according to embodiments.

These methods are preferred for when a heart rate of the patient has been sensed at being less than 100 beats per minute (bpm). The heart rate may be sensed from the time spacing of the QRS complexes, which are equivalent to heart beats, and so on.

According to an operation 910, ECG signals from different channels may be sensed by the measurement circuit. For example a first ECG signal and a second ECG signal may be sensed from respectively a first one and a second one of the available channels. These signals may be sensed over time. For example, previous and recent versions of the first ECG signal and the second ECG signal may be sensed, at different times of course. The recent versions may have been sensed subsequently from the previous versions.

According to another operation 920, a first and a second historical peak amplitudes may be stored in memory 238. The first and the second historical peak amplitudes may represent amplitudes of peaks of previous versions of the first ECG signal and the second ECG signal. The first and the second historical peak amplitudes may have been derived statistically, for example being averages, medians, means, etc. of these amplitudes.

According to another operation 930, a first and a second present peak amplitudes may be detected over respective time durations. The first and the second present peak amplitudes may represent amplitudes of peaks of recent versions of the first ECG signal and the second ECG signal. The first and the second present peak amplitudes may have been derived statistically, for example being averages, medians, means, etc. of these amplitudes. An example is now described.

Figure 10:
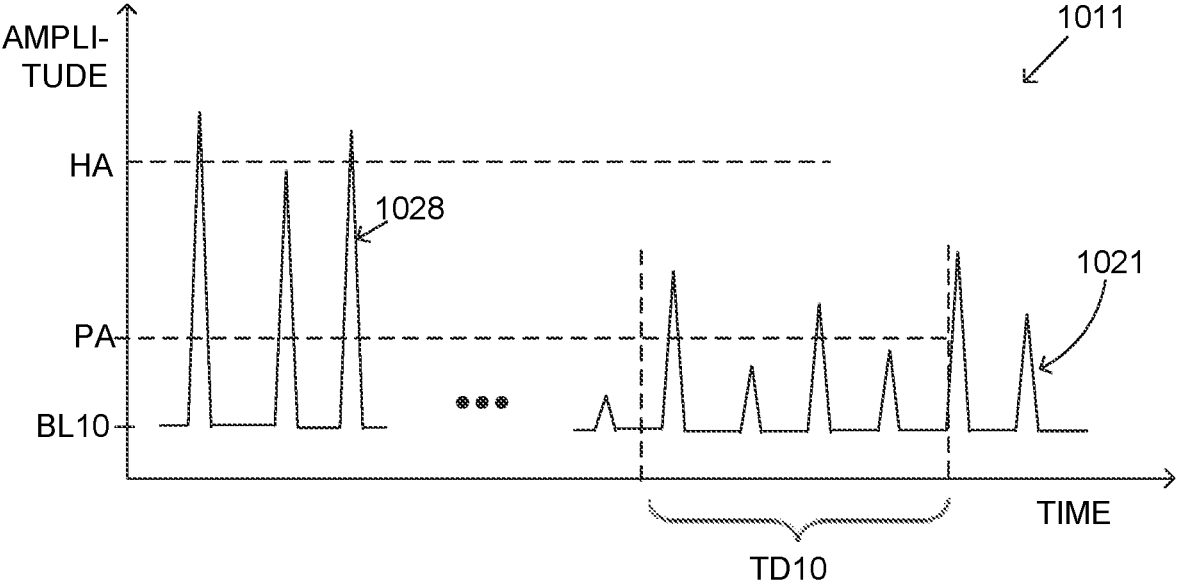
FIG. 10 is a time diagram of a sample previous version and a sample recent version of an ECG signal, whose channel is being evaluated according to embodiments of FIG. 9.

Referring now to FIG. 10, a time diagram 1011 is shown. Diagram 1011 depicts a recent version 1021 of an ECG signal, and a previous version 1028 of the same ECG signal from the same channel. The ECG signal of diagram 1011 may be the first or the second ECG signal whose channel is being evaluated. The evaluation may happen using a portion of recent version 1021 of the ECG signal that occurs over time duration TD10. Again, both the previous and the recent versions are simplified in that only tall peaks are shown, while all other features are shown zeroed-out at a baseline BL10.

For the ECG signal of diagram 1011, a historical peak amplitude HA may represent amplitudes of peaks of previous version 1028 of the ECG signal. In addition, a present peak amplitude PA may represent amplitudes of peaks of recent version 1021 of the ECG signal.

Returning now to FIG. 9, according to another operation 940, a first and a second ratio may be computed. The first and the second ratio may be of the first and second present peak amplitudes over the respective first and second historical peak amplitudes, which have been stored in memory 238. In the example of the signal of FIG. 9, the ratio would be the value of PA over the value of HA (PA/HA). It will be appreciated that these ratios amount to one embodiment of the aforementioned statistics that can be extracted from the ECG signals.

According to another operation 950, it may be evaluated that one of the ECG channels is preferred over the other, for example responsive to the statistics of operation 940. For instance, it may be evaluated that one of the first channel and the second channel is preferred over the other, responsive to one of the first ratio and the second ratio being larger than the other. In some embodiments, the one of the two channels whose ECG signal has the larger ratio is the preferred channel.

Additional operations 960, 970, 980 and 990, may be performed similarly to what was described for operations 760, 770, 780 and 790 of FIG. 7.

Figure 11:
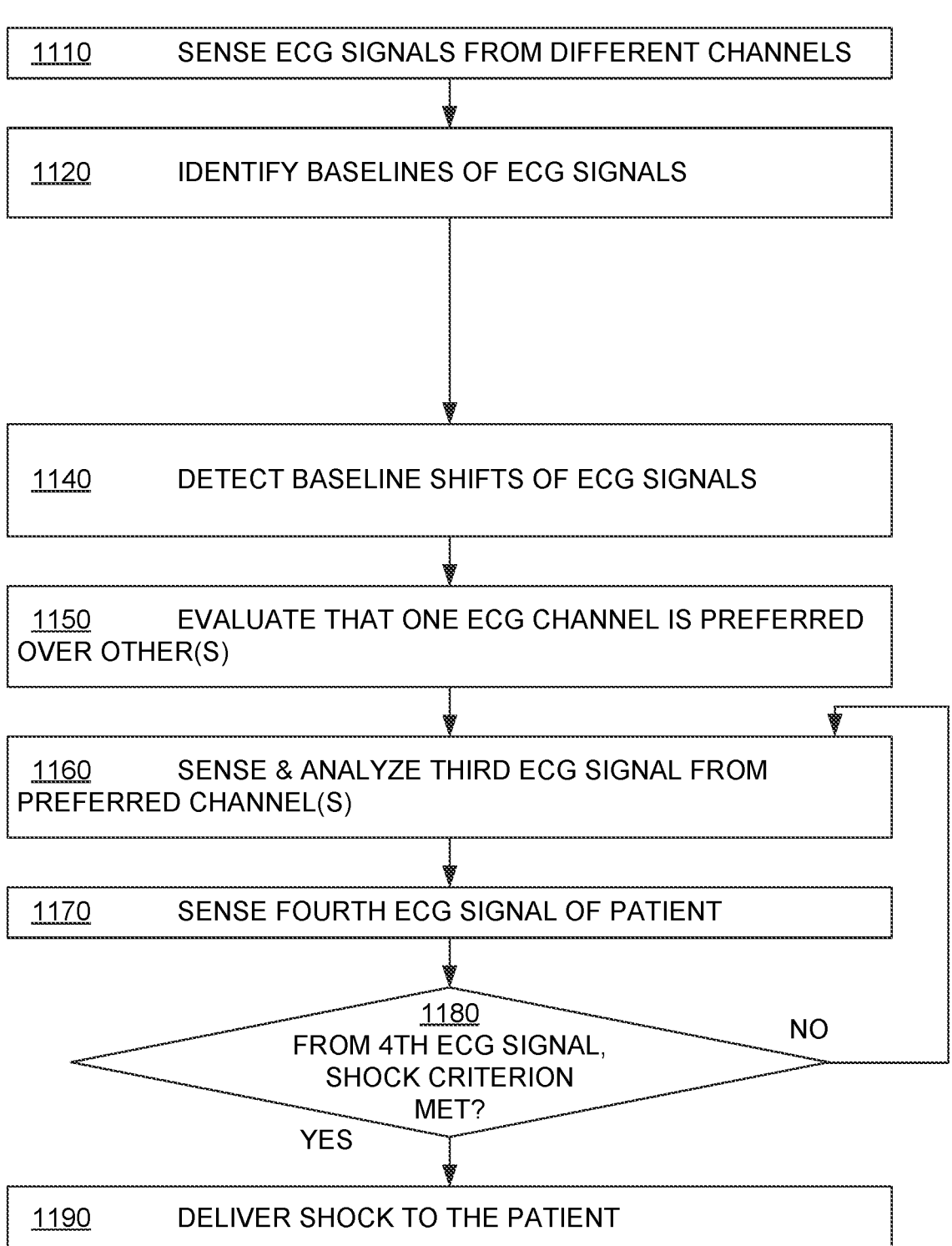
FIG. 11 is a flowchart for illustrating methods according to embodiments.

FIG. 11 shows a flowchart 1100 for describing methods according to embodiments. An operation 1110 may be performed as was described for operation 710, for example to sense a first and a second ECG signal.

According to another operation 1120 in FIG. 11, baselines may be identified of the ECG signals of operation 1110. For example, a first and a second baseline of the first ECG signal and of the second ECG signal may be identified. A baseline can be identified in a number of ways, for example by low-pass filtering that would remove short peaks and capture average slow movement.

According to another operation 1140, shifts of baselines may be detected. For example, a first and a second shift of the first and the second baselines may be detected, preferably over respective time durations. It will be appreciated that these shifts amount to one embodiment of the aforementioned statistics that can be extracted from the ECG signals. An example is now described.

Figure 12:
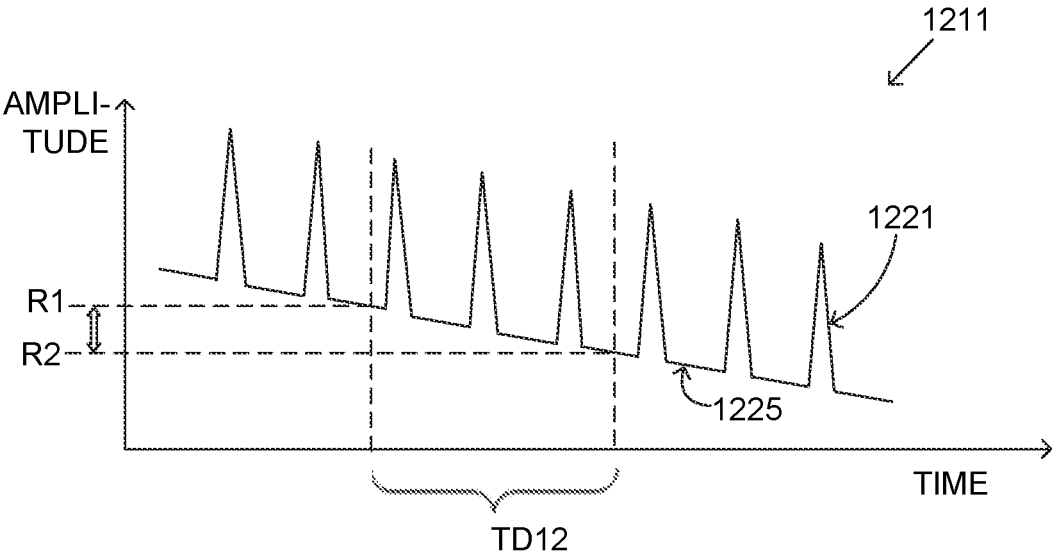
FIG. 12 is a time diagram of a sample ECG signal whose channel is being evaluated according to embodiments of FIG. 11.

Referring now to FIG. 12, a time diagram 1211 is shown. Diagram 1211 depicts a somewhat-simplified ECG signal 1221, which may be the first or the second ECG signal whose channel is being evaluated. Again, the simplification is that only peaks are shown as departures from a detected baseline 1225. It will be observed that baseline 1225 does not remain horizontal, but is gradually shifting to lower values as time passes. This type of shifting is also called baseline wander.

For operation 1140, a time duration TD12 can be considered. The shift of detected baseline 1225 over time duration TD12 is the difference in values R1 and R2.

Returning now to FIG. 11, according to another operation 1150, it may be evaluated that one of the ECG channels is preferred over the other, for example responsive to the statistics of operation 1140. For instance, it may be evaluated that one of the first channel and the second channel is preferred over the other, responsive to one of the first shift and the second shift being smaller than the other. In some embodiments, the one of the two channels whose ECG signal has the smaller shift, of the type seen in FIG. 12, is the preferred channel.

Additional operations 1160, 1170, 1180 and 1190, may be performed similarly to what was described for operations 760, 770, 780 and 790 of FIG. 7.

FIG. 13 shows a flowchart 1300 for describing methods according to embodiments. An operation 1310 may be performed as was described for operation 710, for example to sense a first and a second ECG signal. And an operation 1320 may be performed as was described for operation 1120, for example to identify a first baseline of the first ECG signal, and a second baseline of the second ECG signal.

According to another operation 1330, the ECG signals sensed at operation 1310 may be high-pass filtered. For example, the first ECG signal and the second ECG signal may be filtered with a high-pass filter to derive a first high-pass filtered (HPF) ECG signal and a second HPF ECG signal.

According to another operation 1340, dwell times during which the HPF ECG signals are near the baselines of operation 1320 can be measured. This criterion can become a measurable statistic in a number of ways. For example, for the first HPF ECG signal and for the second HPF ECG signal, dwell times can be measured over respective time durations. These dwell times can be time intervals within the time durations, during which the first HPF ECG signal and the second HPF ECG signal are closer than a threshold to the identified respective baselines. In some embodiments, these dwell times are measured as fractions of the respective time durations. It will be appreciated that these dwell times amount to one embodiment of the aforementioned statistics that can be extracted from the ECG signals. An example is now described.

Figure 14:
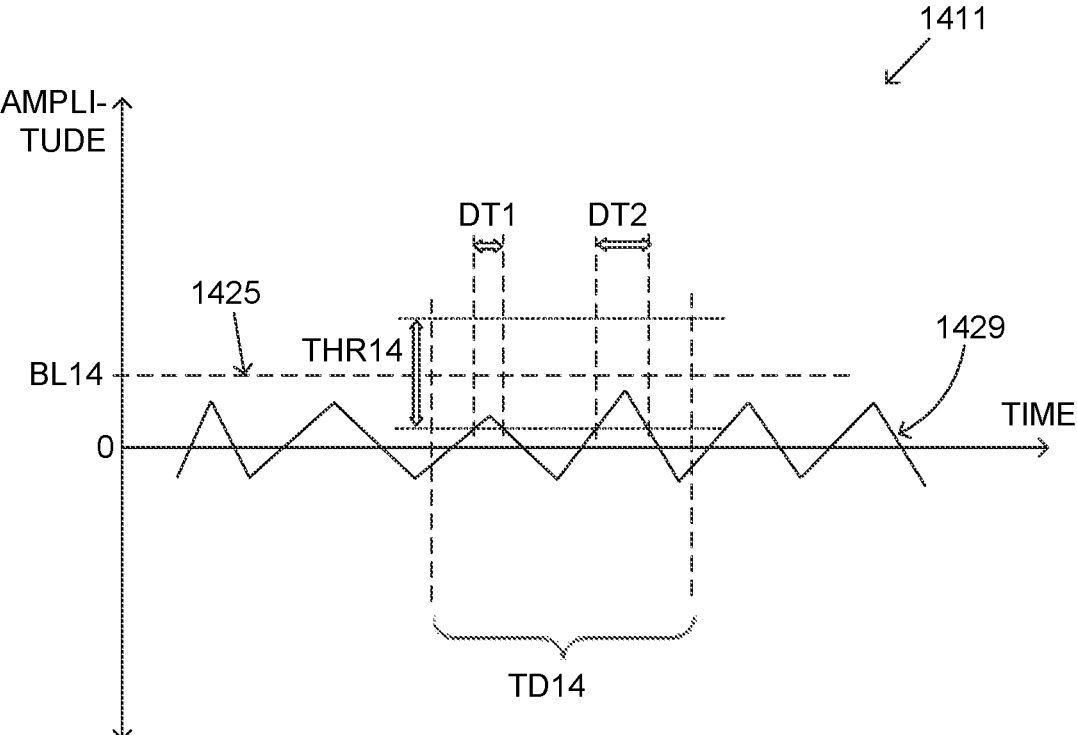
FIG. 14 is a time diagram of a sample HPF ECG signal whose channel is being evaluated according to embodiments of FIG. 13.

Referring now to FIG. 14, a time diagram 1411 is shown. A time duration TD14 is designated on the horizontal time axis. Differently, diagram 1411 does not depict an ECG signal, so as not to clutter the drawing. Still, diagram 1411 is about an ECG signal, which may be the first or the second ECG signal whose channel is being evaluated.

Diagram 1411 does depict a baseline 1425 of the not-shown ECG signal. Baseline 1425 is shown as having a positive DC offset, i.e. being above the zero line. In this example, baseline 1425 is shown as a straight line, but that is only for simplicity. The baseline could be shifting, for example as seen in FIG. 12, in which case this description still applies.

Diagram 1411 also depicts a high-pass filtered (HPF) ECG signal 1429, which may be the first or the second HPF ECG signal that has been derived from the first or the second ECG signal according to operation 1330. The high pass filtering has eliminated, from HPF ECG signal 1429, the DC offset and also any baseline shift or wander.

For measuring how close HPF ECG signal 1429 is to baseline 1425 in a way that gives a number, an amplitude threshold THR14 can be selected as a zone around baseline 1425 of the ECG signal from which HPF ECG signal 1429 was derived. In the example of FIG. 14, the dwell time is found by adding time intervals DT1 and DT2. These time intervals are the only times in which both criteria are met: they occur within time duration TD14; and, during time intervals DT1 and DT2, HPF ECG signal 1429 has a value within the zone that THR14 defines around baseline 1425.

The dwell time of time intervals DT1 and DT2 can also be measured as a fraction of time duration TD14. And this can be the dwell time about the ECG signal of an ECG channel, which can be compared with the dwell times for other channels.

The dwell time measurement can be made with some practical adjustments, for example about selecting the value of THR14. It can be chosen so it gives a meaningful number for the dwell time for at least one of the HPF ECG signals. If too high, the dwell time will be 100% of time duration TD14, and if too low the dwell time will be 0%. A meaningful number will give a good fraction. In the shown example of FIG. 14, the dwell time fraction is about 31%. Once that is accomplished for one channel, then it can be compared with the others; and the answers are then useful even if these others are measured to be 0% or 100%. Ties between channels can then be resolved, etc.

Returning now to FIG. 13, according to another operation 1350, it may be evaluated that one of the ECG channels is preferred over the other, for example responsive to the statistics of operation 1340. For instance, it may be evaluated that one of the first channel and the second channel is preferred over the other, responsive to one of the first HPF ECG signal and the second HPF ECG signal having a larger measured dwell time than the other. In some embodiments, the one of the two channels whose HPF ECG signal has the larger dwell time, of the type seen in FIG. 14, is the preferred channel.

Additional operations 1360, 1370, 1380 and 1390, may be performed similarly to what was described for operations 760, 770, 780 and 790 of FIG. 7.

FIG. 15 shows a flowchart 1500 for describing methods according to embodiments. An operation 1510 may be performed as was described for operation 710, for example to sense a first and a second ECG signal. Another operation 1530 may be performed as was described for operation 1330, for example to derive a first highpass filtered (HPF) ECG signal and a second HPF ECG signal.

According to another operation 1540, certain peaks of the first HPF ECG signal and of the second HPF ECG signal may be counted, over respective time durations. In embodiments, the counted peaks are those that have widths narrower than a threshold width. It will be appreciated that these counted peaks amount to one embodiment of the aforementioned statistics that can be extracted from the ECG signals. An example is now described.

Figure 16:
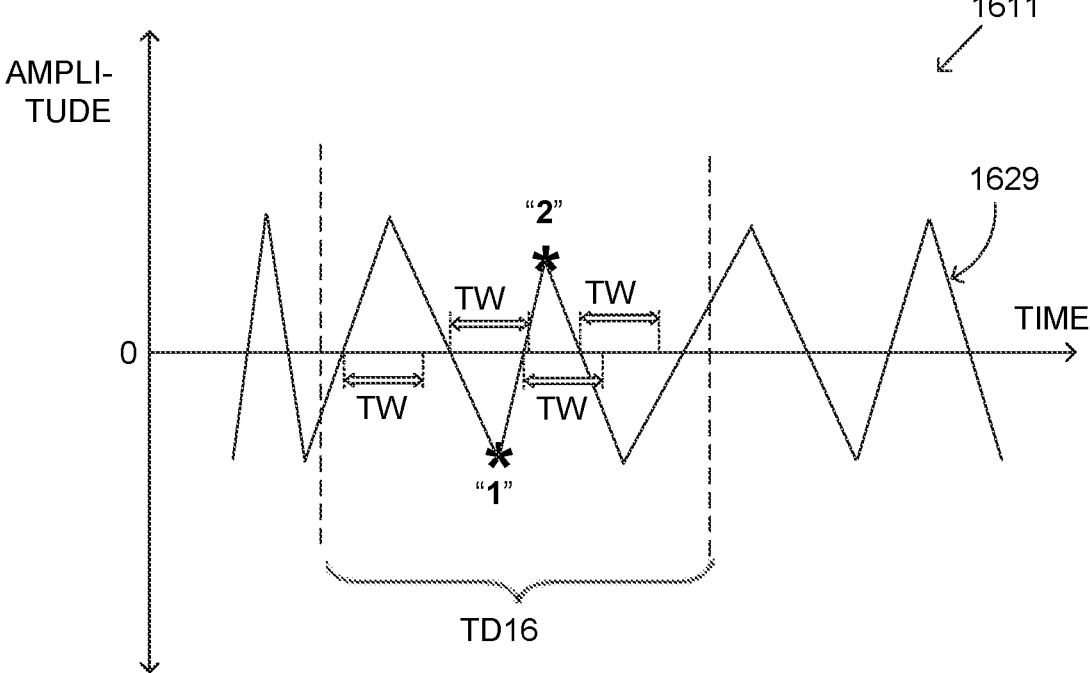
FIG. 16 is a time diagram of a sample HPF ECG signal whose channel is being evaluated according to embodiments of FIG. 15.

Referring now to FIG. 16, a time diagram 1611 is shown, and a time duration TD16 is designated on the horizontal time axis. As with FIG. 14, FIG. 16 does not depict an ECG signal, but is still about an ECG signal that may be the first or the second ECG signal whose channel is being evaluated.

Diagram 1611 depicts a high-pass filtered (HPF) ECG signal 1629, which may be the first or the second HPF ECG signal that has been derived from the first or the second ECG signal according to operation 1530. HPF ECG signal 1629 has four peaks within time duration TD16, with alternating directions: up, down, up, down. Each of these peaks has a width. In this particular example, the width is defined to be the width at the zero level, while other definitions of width are also possible.

In diagram 1611, each of the widths of the four peaks within time duration TD16 is compared against a threshold width TW. The width of the first and of the last of these peaks is larger than TW, meaning the next zero crossing happens after time TW, and therefore these two peaks are not counted. The width of the other two peaks is less than TW, and therefore these two peaks are counted, as indicated by asterisks on the drawing. In this drawing, therefore, for this signal two such narrow peaks "1", "2" are counted, and the total narrow peak count is 2.

Returning now to FIG. 15, according to another operation 1550, it may be evaluated that one of the ECG channels is preferred over the other, for example responsive to the statistics of operation 1540. For instance, it may be evaluated that one of the first channel and the second channel is preferred over the other, responsive to one of the first HPF ECG signal and the second HPF ECG signal having fewer of the narrow counted peaks than the other. In some embodiments, the one of the two channels whose ECG signal has the fewer narrow peaks, of the type seen in FIG. 16, is the preferred channel.

Additional operations 1560, 1570, 1580 and 1590, may be performed similarly to what was described for operations 760, 770, 780 and 790 of FIG. 7.

Figure 17:
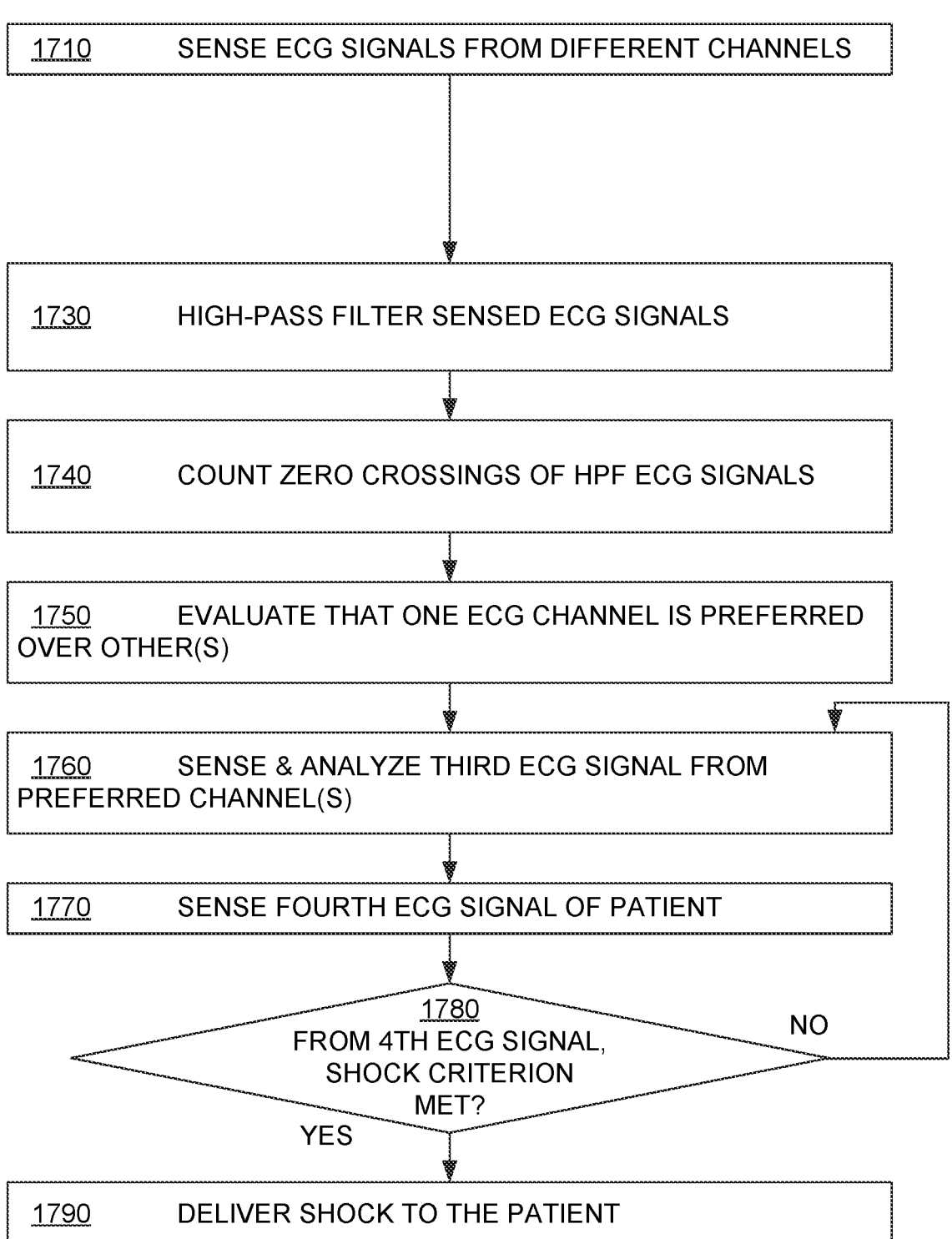
FIG. 17 is a flowchart for illustrating methods according to embodiments.

FIG. 17 shows a flowchart 1700 for describing methods according to embodiments. An operation 1710 may be performed as was described for operation 710, for example to sense a first and a second ECG signal. Another operation 1730 may be performed as was described for operation 1330, for example to derive a first high-pass filtered (HPF) ECG signal and a second HPF ECG signal.

According to another operation 1740, zero crossings of the HPF ECG signals may be counted over respective time durations. For instance, zero crossings of the first HPF ECG signal and of the second HPF ECG signal may be counted. It will be appreciated that these zero crossings counts amount to one embodiment of the aforementioned statistics that can be extracted from the ECG signals. An example is now described.

Figure 18:
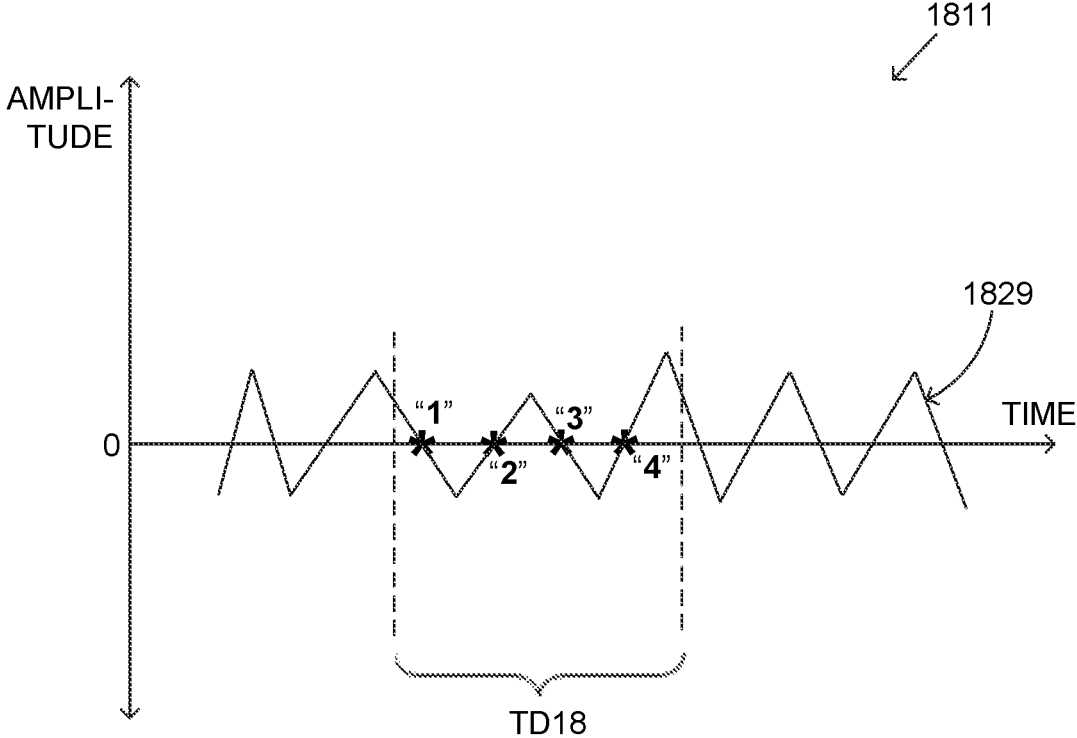
FIG. 18 is a time diagram of a sample HPF ECG signal whose channel is being evaluated according to embodiments of FIG. 17.

Referring now to FIG. 18, a time diagram 1811 is shown, and a time duration TD18 is designated on the horizontal time axis. As with FIG. 14, FIG. 18 does not depict an ECG signal, but is still about an ECG signal that may be the first or the second ECG signal whose channel is being evaluated.

Diagram 1811 depicts a high-pass filtered (HPF) ECG signal 1829, which may be the first or the second HPF ECG signal that has been derived from the first or the second ECG signal according to operation 1730. HPF ECG signal 1829 is shown as having only upward-directed peaks and downward-directed peaks in this example.

Within time duration TD18, HPF ECG signal 1829 has four zero crossings indicated by asterisks, i.e. locations where signal 1829 intersects the zero line. So, in this drawing, for this signal, four zero crossings "1", "2", "3", "4" are counted, and the total count is 4.

Returning now to FIG. 17, according to another operation 1750, it may be evaluated that one of the ECG channels is preferred over the other, for example responsive to the statistics of operation 1740. For instance, it may be evaluated that one of the first channel and the second channel is preferred over the other, responsive to one of the first HPF ECG signal and the second HPF ECG signal having fewer of the counted zero crossings than the other. In some embodiments, the one of the two channels whose ECG signal has the fewer zero crossings, of the type seen in FIG. 18, is the preferred channel.

Additional operations 1760, 1770, 1780 and 1790, may be performed similarly to what was described for operations 760, 770, 780 and 790 of FIG. 7.

FIG. 19 shows a flowchart 1900 for describing methods according to embodiments. An operation 1910 may be performed as was described for operation 710, for example to sense a first and a second ECG signal.

According to another operation 1940, heart rates may be determined from the sensed ECG signals. For example, a first heart rate and a second heart rate may be determined, optionally over respective time durations. It will be appreciated that these heart rates amount to one embodiment of the aforementioned statistics that can be extracted from the ECG signals.

In such embodiments, the heart rate may be determined from detected peaks that are presumed to be QRS peaks, such as those seen in FIG. 5. It is preferred that a QRS detector is designed to be very sensitive, so that a QRS complex would be rarely missed. This may correspond with operation 740 of FIG. 7 and with threshold THR8 of FIG. 8, where threshold THR8 is set to operate as such a sensitive QRS detector.

According to another operation 1950, it may be evaluated that one of the ECG channels is preferred over the other, for example responsive to the statistics of operation 1940. For instance, it may be evaluated that one of the first channel and the second channel is preferred over the other, responsive to one of the first heart rate and the second heart rate being less than the other. This could be because noise has interposed peaks that were mistaken as QRS peaks, and have yielded a falsely higher heart rate.

Additional operations 1960, 1970, 1980 and 1990, may be performed similarly to what was described for operations 760, 770, 780 and 790 of FIG. 7.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and nonobvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

The invention claimed is:

1. An external defibrillator, comprising:
a pulse sensor configured to detect a first pulse of a subject during a first time and a second pulse of the subject during a second time;
a discharge circuit configured to output an electrical shock to the subject; and
a processor configured to:
determine that the second pulse is weaker than the first pulse;
identify, in a first electrocardiogram (ECG) channel detected during the first time, a first number of peaks with widths narrower than a threshold width;
identify, in a second ECG channel detected during the first time, a second number of peaks with widths narrower than the threshold width;
determine that the first number of peaks is higher than the second number of peaks;
in response to determining that the second pulse is weaker than the first pulse and determining that the first number of peaks is higher than the second number of peaks, determine that the first ECG channel detected during the second time is indicative of ventricular fibrillation (VF); and
in response to determining that the first ECG channel detected during the second time is indicative of VF, cause the discharge circuit to output the electrical shock to the subject.

2. The external defibrillator of claim 1, wherein the first ECG channel corresponds to a first vector, and wherein the second ECG channel corresponds to a second vector, the first vector being nonparallel to the second vector.

3. The external defibrillator of claim 1, wherein the pulse sensor is further configured to detect a third pulse of the subject during a third time, and wherein the processor is further configured to:
in response to causing the discharge circuit to output the electrical shock, determine that the third pulse is stronger than the second pulse; and
in response to determining that the third pulse is stronger than the second pulse, determine that a condition of the subject is improving.

4. A medical device, comprising:
a sensor configured to detect a parameter; and
a processor configured to:
determine, in a first ECG channel detected from a subject during a first time, a first selection criterion;
determine, in a second ECG channel detected from the subject during the first time, a second selection criterion;

determine that the first selection criterion is preferred over the second selection criterion;

in response to determining that the first selection criterion is preferred over the second selection criterion, determine whether the first ECG channel detected during a second time is indicative of a condition;

determine, by analyzing the parameter, whether the first ECG channel accurately reflects a state of the subject; and in response to determining whether the first ECG channel detected during the second time is indicative of the condition and determining whether the first ECG channel accurately reflects the state of the subject, output a determination of whether to shock the subject.

5. The medical device of claim 4, wherein the sensor is configured to detect the parameter during the second time.

6. The medical device of claim 4, wherein the parameter is a patient parameter detected from the subject, a system parameter, or an environmental parameter.

7. The medical device of claim 6, wherein the patient parameter comprises a blood oxygen level, a blood flow, a blood pressure, a blood perfusion, a pulsatile change in light transmission or reflection properties of perfused tissue, heart sounds, a heart wall motion, breathing sounds, a pulse, an ejection fraction, a stroke volume, cardiac output, or a movement.

8. The medical device of claim 6, wherein the system parameter comprises a system identification, a battery status, system date, a system time, a report of self-testing, a record of data entered, a record of an episode, or a record of an intervention, or wherein the environmental parameter comprises a temperature or a humidity.

9. The medical device of claim 4, wherein the first selection criterion or the second selection criterion comprises a baseline shift, a dwell time, a ratio of peak amplitude, a number of peaks with widths narrower than a threshold width, a number of peaks with amplitudes above a threshold amplitude, a number of zero crossings, or a heart rate.

10. The medical device of claim 4, wherein the processor is configured to:

determine whether the first ECG channel detected during the second time is indicative of the condition by determining that the first ECG channel detected during the second time is indicative of VF or ventricular tachycardia (VT);

determine whether the first ECG channel accurately reflects the state of the subject by determining that the first ECG channel does not accurately reflect the state of the subject; and output the determination by outputting the determination to not shock the subject.

11. The medical device of claim 4, wherein the parameter is a first parameter detected during the second time, wherein the sensor is configured to detect a second parameter during a third time, and wherein the processor is configured to:

determine whether the first ECG channel detected during the second time is indicative of the condition by determining that the first ECG channel detected during the second time is indicative of VF or VT;

determine, by analyzing the first parameter, whether the first ECG channel accurately reflects the state of the subject by:

comparing the first parameter and the second parameter; and in response to comparing the first parameter and the second parameter, determining that the first ECG channel accurately reflects the state of the subject; and output the determination by outputting the determination to shock the subject.

12. A method, comprising:

determining whether a non-ECG parameter is indicative of a condition of a subject;

determining, in a first ECG channel detected during a first time, a first selection criterion;

determining, in a second ECG channel detected during the first time, a second selection criterion;

determining that the first selection criterion is preferred over the second selection criterion;

in response to determining that the first selection criterion is preferred over the second selection criterion, determining whether the first ECG channel detected during a second time is indicative of the condition; and in response to determining whether the non-ECG parameter is indicative of the condition and determining whether the first ECG channel detected at the second time is indicative of the condition, outputting a determination of whether to shock the subject.

13. The method of claim 12, wherein comparing the first selection criterion and the second selection criterion comprises:

comparing a first baseline shift of the first ECG channel detected during the first time and a second baseline shift of the second ECG channel detecting during the first time;

comparing a first dwell time of the first ECG channel detected during the first time and a second dwell time of the second ECG channel detected during the first time;

comparing a first ratio of peak amplitude of the first ECG channel detected during the first time and a second ratio of the second ECG channel detected during the first time;

comparing a first number of peaks with widths narrower than a threshold width of the first ECG channel detected during the first time and a second number of peaks with widths narrower than a threshold width of the second ECG channel detected during the first time;

comparing a first number of peaks with amplitudes above a threshold amplitude of the first ECG channel detected during the first time and a second number of peaks with amplitudes above a threshold amplitude of the second ECG channel detected during the first time;

comparing a first number of zero crossings of the first ECG channel detected during the first time and a second number of zero crossings of the second ECG channel detected during the first time; or comparing a first heart rate determined from the first ECG channel detected during the first time and a second heart rate determined from the second ECG channel detected during the first time.

14. The method of claim 12, wherein determining that the non-ECG parameter is indicative of the condition comprises determining that the non-ECG parameter is not indicative of VF or VT;

wherein determining whether the first ECG channel detected during the second time is indicative of the condition comprises determining that the first ECG channel detected during the second time is indicative of VF or VT; and wherein outputting the determination comprises outputting the determination to not shock the subject.

15. The method of claim 12, wherein determining that the non-ECG parameter is indicative of the condition comprises determining that the non-ECG parameter is indicative of VF or VT;

wherein determining whether the first ECG channel detected during the second time is indicative of the condition comprises determining that the first ECG channel detected during the second time is indicative of VF or VT; and wherein outputting the determination comprises outputting the determination to shock the subject.

16. The method of claim 12, wherein the non-ECG parameter is a first non-ECG parameter detected at the first time, the method further comprising:

determining whether a second non-ECG parameter detected at the second time is indicative of the condition; and in response to determining whether the second non-ECG parameter is indicative of the condition, determining that a state of the subject is deteriorating, wherein determining that the first ECG channel detected during the second time is indicative of the condition comprises determining that the first ECG channel detected during the second time is indicative of VF or VT, and wherein outputting the determination comprises outputting a determination to shock the subject.

17. The method of claim 12, wherein the non-ECG parameter is a first non-ECG parameter detected at the first time, the method further comprising:

detecting the first ECG channel during the first time and the second time;

detecting the second ECG channel during the first time;

determining whether a second non-ECG parameter detected at a third time is indicative of the condition;

in response to determining whether the second non-ECG parameter is indicative of the condition, determining that a state of the subject is deteriorating; and in response to determining that the condition of the subject is deteriorating, detecting the first ECG channel during the second time.

18. The method of claim 12, further comprising:

in response to outputting the determination of whether to shock the subject, causing a discharge circuit to output an electrical shock to the subject.

19. The method of claim 12, wherein the non-ECG parameter is a patient parameter detected from the subject, a system parameter, or an environmental parameter.

20. The method of claim 12, wherein the non-ECG parameter is a first non-ECG parameter detected during the second time, the method further comprising:

identifying a second non-ECG parameter detected during a third time;

determine whether the first ECG channel detected during the second time is indicative of the condition by determining that the first ECG channel detected during the second time is indicative of VF or VT;

determine, by analyzing the first non-ECG parameter, whether the first ECG channel accurately reflects a state of the subject by:

comparing the first non-ECG parameter and the second non-ECG parameter; and in response to comparing the first non-ECG parameter and the second non-ECG parameter, determining that the first ECG channel accurately reflects the state of the subject; and output the determination by outputting the determination to shock the subject.

* * * * *